(12) United States Patent
Reed

(10) Patent No.: US 9,018,193 B2
(45) Date of Patent: Apr. 28, 2015

(54) AQUEOUS DRUG DELIVERY SYSTEM

(75) Inventor: Kyle A. Reed, Lakeland, FL (US)

(73) Assignee: Bev-Rx, Inc., Scituate, MA (US)

( * ) Notice: Subject to any disclaimer, the term of this patent is extended or adjusted under 35 U.S.C. 154(b) by 0 days.

(21) Appl. No.: 13/231,150

(22) Filed: Sep. 13, 2011

(65) Prior Publication Data

US 2012/0122823 A1 May 17, 2012

Related U.S. Application Data

(60) Provisional application No. 61/382,098, filed on Sep. 13, 2010.

(51) Int. Cl.

| | | |
|---|---|---|
| *A61K 31/616* | (2006.01) | |
| *A61K 31/167* | (2006.01) | |
| *A61P 43/00* | (2006.01) | |
| *A61K 31/192* | (2006.01) | |
| *A23L 1/22* | (2006.01) | |
| *A23L 2/52* | (2006.01) | |
| *A61K 9/00* | (2006.01) | |
| *A61K 9/16* | (2006.01) | |
| *A61K 47/48* | (2006.01) | |
| *B82Y 5/00* | (2011.01) | |

(52) U.S. Cl.
CPC ............ *A61K 31/167* (2013.01); *A23L 1/22075* (2013.01); *A23L 2/52* (2013.01); *A61K 9/0095* (2013.01); *A61K 9/1652* (2013.01); *A61K 31/192* (2013.01); *A61K 31/616* (2013.01); *A61K 47/48969* (2013.01); *B82Y 5/00* (2013.01)

(58) Field of Classification Search
USPC .................. 514/165, 569, 630, 570
See application file for complete search history.

(56) References Cited

U.S. PATENT DOCUMENTS

| | | | |
|---|---|---|---|
| 4,861,760 A | 8/1989 | Mazuel et al. | |
| 5,362,860 A | 11/1994 | Huang et al. | |
| 5,633,030 A | 5/1997 | Marrs et al. | |
| 5,776,431 A | 7/1998 | Galat | |
| 5,846,566 A | 12/1998 | Burguiere et al. | |
| 5,912,005 A | 6/1999 | Lanza et al. | |
| 6,306,843 B1 | 10/2001 | Burghart et al. | |
| 6,319,535 B1 | 11/2001 | Shaw | |
| 7,052,725 B2 | 5/2006 | Chang et al. | |
| 7,141,555 B2 | 11/2006 | Jacobs et al. | |
| 7,160,565 B2 | 1/2007 | Rifkin | |
| 7,713,551 B2 | 5/2010 | McGurk et al. | |
| 7,727,552 B1 | 6/2010 | Ukai et al. | |
| 2002/0032217 A1 | 3/2002 | Fanara et al. | |
| 2003/0082272 A1 | 5/2003 | Bouwmeesters et al. | |
| 2004/0019012 A1* | 1/2004 | Singh et al. ................. | 514/58 |
| 2005/0089577 A1 | 4/2005 | Yokoyama et al. | |
| 2006/0134148 A1 | 6/2006 | Hollenbeck | |
| 2007/0053939 A1 | 3/2007 | Yokoyama et al. | |
| 2007/0092561 A1 | 4/2007 | Milne | |
| 2007/0231367 A1 | 10/2007 | Fukui | |
| 2007/0259931 A1 | 11/2007 | Haldar et al. | |
| 2008/0044481 A1 | 2/2008 | Harel | |
| 2008/0075784 A1 | 3/2008 | Friesen et al. | |
| 2008/0089940 A1 | 4/2008 | Omidian et al. | |
| 2008/0299199 A1 | 12/2008 | Bar-Shalom et al. | |
| 2009/0011019 A1 | 1/2009 | Jahagirdar et al. | |
| 2009/0061048 A1 | 3/2009 | Kohane et al. | |
| 2009/0104251 A1 | 4/2009 | Lee | |
| 2009/0155409 A1* | 6/2009 | Sexton et al. ................. | 426/2 |
| 2009/0215735 A1 | 8/2009 | Castillo et al. | |
| 2009/0306225 A1 | 12/2009 | Lichter et al. | |
| 2010/0015227 A1 | 1/2010 | Nussinovitch et al. | |
| 2010/0019403 A1 | 1/2010 | Beco Pinto Reis et al. | |
| 2011/0038942 A1 | 2/2011 | Livney | |

FOREIGN PATENT DOCUMENTS

| | | |
|---|---|---|
| EP | 2 201 956 | 6/2010 |
| WO | WO 00/71137 | 11/2000 |
| WO | WO 01/66601 | 9/2001 |
| WO | WO 2004/009053 | 1/2004 |
| WO | WO 2005/023176 | 3/2005 |
| WO | WO 2005/072709 | 8/2005 |
| WO | WO 2005/107713 | 11/2005 |
| WO | WO 2007/129926 | 11/2007 |
| WO | WO 2008/012329 | 1/2008 |
| WO | WO 2009/022761 | 2/2009 |
| WO | WO 2009/029406 | 3/2009 |
| WO | WO 2009/082227 | 7/2009 |

(Continued)

OTHER PUBLICATIONS

DahNan D. Chow, Adel H. Karara, Characterization, dissolution and bioavailability in rats of ibuprofen-β-cyclodextrin complex system, International Journal of Pharmaceutics vol. 28, Issues 2-3, Feb. 1986, pp. 95-101.*

MuscleTech CELL-TECH Hardcore Pro Series.*

D. Ziegler, M. Reljanovic, H. Mehnert, F. A. Gries, α-Lipoic acid in the treatment of diabetic polyneuropathy in Germany: Current evidence from clinical trials, Exp Clin Endocrinol Diabetes 1999; 107(7): 421-430.*

Agnihotri, Sunil A. et al.; "Controlled release of cephalexin through gellan gum beads: Effect of formulation parameters on entrapment efficiency, size, and drug release;" *European Journal of Pharmaceutics and Biopharmaceutics*; 2006; pp. 249-261; vol. 63.

(Continued)

*Primary Examiner* — Sreeni Padmanabhan
*Assistant Examiner* — Jason A Deck
(74) *Attorney, Agent, or Firm* — Walter C. Frank; Feldman Gale, P.A.

(57) ABSTRACT

Novel water stable pharmaceutical compositions, their liquid form oral pharmaceutical compositions and kits thereof, rehydration beverages containing these water stable pharmaceutical compositions methods of manufacture and methods of use thereof are disclosed. The novel aqueous delivery systems are useful, inter alia, as alternative pharmaceutical dosing agents to tablets, capsules and other forms of delivering medication to a mammalian host in need thereof.

43 Claims, 14 Drawing Sheets

(56) References Cited

FOREIGN PATENT DOCUMENTS

| WO | WO 2009/098520 | 8/2009 |
|----|----------------|--------|
| WO | WO 2010/014661 | 2/2010 |

OTHER PUBLICATIONS

Aguilar, M. R., et al.; "Smart Polymers and Their Applications as Biomaterials;" Topics in Tissue Engineering; Biomaterials; Chapter 6; 2007; pp. 1-27; vol. 3.
Bakar, SK et al.; "Stability of aspirin in different media;" *Journal of Pharm. Sci.*; Sep. 1983; pp. 1024-1026; vol. 72; No. 9 (Abstract Only).
Challa, Rajeswari, et al.; "Cyclodextrins in Drug Delivery: An Updated Review;" *AAPS PharmSciTech*; 2005; pp. E329-E357; vol. 6; No. 2; article 43.
Choi, Hee-Sook; "Molecular Recognition: α-Cyclodextrin and Aspirin Inclusion Complexation;" *Bull. Korean Chem. Soc.*; 1992; pp. 474-479; vol. 13; No. 5.
Coviello, Tommasina, et al.; "Polysaccharide hydrogels for modified release formulations;" *Journal of Controlled release*; 2007; pp. 5-24; vol. 119.
Kelcogel Gellan Gum Book; $5^{th}$ Edition; 2007; 32 pages.
Dea, I. C. M., et al.; "Synergistic Xanthan Gels;" Jun. 1, 1977; pp. 174-182.
Diener, HC, et al.; "The fixed combination of acetylsalicylic acid, paracetamol and caffeine is more effective than single substances and dial combination for the treatment of headache: a multicentre, randomized, double-blind, single-dose, placebo-controlled parallel group study;" *Cephalalgia*; 2005; pp. 776-787; vol. 25.
Dong, C. et al.; "Acacia-Gelatin Microencapsulated Liposomes: Preparation, Stability, and Release of Acetylsalicylic Acid;" *Pharmaceutical Research*; Jan. 1993; pp. 141-146; vol. 10; No. 1 (Abstract Only).
Ettner, Nrbert PhD, et al.; "How Sweet It Is! Reducing the bitterness of Drugs;" Sep. 2006; pp. 1-6.
Fukahori, Takanori, et al.; "Dynamic Study of Interaction between β-Cyclodextrin and Aspirin by the Ultrasonic Relaxation Method;" *J. Phys. Chem. B.*; 2006; pp. 4487-4491; vol. 110; No. 9.
Han, Jung H, et al.; "Lactitol-Based Poly(ether polyol) Hydrogels for Controlled Release Chemical and Drug Delivery Systems;" *J. Agric. Food Chem.*; 2000; pp. 5278-5282; vol. 48.
Hladon, Teresa, et al.; "Stability of Ibuprofen in its Inclusion Complex with β-Cyclodextrin;" *Journal of Inclusion Phenomena and Macrocyclic Chemistry*; 2000; pp. 1-8; vol. 36.
Jain, Anekant, et al.; "Perspectives of Biodegradable Natural Polysaccharides for Site-Specific Drug Delivery to the Colon;" *J. Pham. Pharmaceut. Sci.*; 2007; pp. 86-128; vol. 10. No. 1.
Jinbo, Yuji, et al.; "Higher order structures of gellan gum gels and the gelation mechanism;" 2000; one page; http://pfwww.kek.jp/acr2000/b/y00p139.pdf.
Kedzierewics, F., et al.; "Effect of the formulation on the in-vitro release of propranolol from gellan beads;" *International Journal of Pharmaceutics*; 1999; pp. 129-136; vol. 178.
Koontz, John L.; "Improved Properties of Natamycin Upon Formation of Cyclodextrin Inclusion Complexes;" Feb. 6, 2003; 139 pages.
Kubo, Wataru, et al.; "Oral sustained delivery of paracetamol from in situ-gelling gellan and sodium alginate formulations;" *International Journal of Pharmaceutics*; 2003; pp. 55-64; vol. 258.
Masteiková, Rūta, et al.; "Stimuli-sensitive hydrogels in controlled and sustained drug delivery;" *Medicina*; 2003; pp. 19-24; vol. 39; No. 2.
Malmsten, Martin; "Soft drug delivery systems;" *Soft Matter*; 2006; pp. 760-769; vol. 2.
Miyazaki, Ahozo, et al.; "The effect of taste masking agents on in situ gelling pectin formulations for oral sustained delivery of paracetamol and ambroxol;" *International Journal of Pharmaceutics*; 2005; pp. 38-49; vol. 297.
Moritaka, H., et al.; "Particle and matrix gels of gellan gum: effects of filler particles on rhelogical properties of matrix gels;" *Food Hydrocolloids*; 2002; pp. 175-182; vol. 16.

Nickerson, M.T., et al.; "Rheological properties of gellan solutions: effect of calcium ions and temperature on pre-gel formation;" *Food Hydrocolloids*; 2003; pp. 577-583; vol. 17.
Nishikawa, Sadakatsu, et al.; "Ultrasonic Relaxation Associated with Inclusion Complex of Drugs and β-Cyclodextrin;" Department of Chemistry and Applied Chemistry, Faculty of Science and Engineering, Saga University; 2006 (Abstract Only).
Nitta, Yoko, et al.; "Gelation and gel properties of polysaccharides gellan gum and tamarind xyloglucan;" *J. Biol. Macromol.*; 2005; pp. 47-52; vol. 5. No. 3.
Nitta, Yoko, et al.; "The reinforcement of gellan gel network by the immersion into salt solution;" *International Journal of Biological Macromolecules*; 2006; pp. 145-147; vol. 38.
Norton, Sylvain, et al.; "Gellan gum gel as entrapment matrix for high temperature fermentation processes: a rheological study;" *Biotechnology Techniques*; 1990; p. 1 only; vol. 4; No. 5.
Nussinovitch, A., et al.; "Unique shape, surface and porosity of dried electrified alginate gels;" *Food Hydrocolloids*; 2008; pp. 364-372; vol. 22.
Perlovich, German L., et al; "Solvation and Hydration Characteristics of Ibuprofen and Acetylsalicylic Acid;" *AAPS PharmSci.*; 2004; pp. 1-9; vol. 6; No. 1; article 3.
Qian, Junhong, et al.; "Effect of Microemulsion Structures on the Hydrolysis of Acetylsalicylic Acid;" *Journal of Dispersion Science and Technology*; Aug. 2001; pp. 541-549; vol. 22; issue 6 (Abstract Only).
Renard, Denis, et al.; "The gap between food gel structure, texture and perception;" *Food Hydrocolloids*; 2006; pp. 423-431; vol. 20.
Sewald, Mark, et al.; "Food Product Shelf Life;" Medallion Laboratories Analytical Progress; pp. 1-10.
Some, Issa T., et al.; "Stability Parameter Estimation at Ambient Temperature From Studies at Elevated Temperatures;" *Journal of Pharmaceutical Sciences*; Nov. 2001; pp. 1759-1766; vol. 90; No. 11.
Szejtli, J., et al.; "Elimination of bitter, disgusting tastes of drugs and foods by cyclodextrins;" *European Journal of Pharmaceutics and Biopharmaceutics*; 2005; pp. 115-125; vol. 61.
Tamagawa, Hirohisa, et al.; "An interpretation of amphoteric gel hardness variation through potential and hardness measurement;" *Journal of Colloid and Interface Science*; 2004; pp. 107-112; vol. 275.
Tang, J., et al.; "Gelling temperature, gel clarity and texture of gellan gels containing fructose or sucrose;" *Carbohydrate Polymers*; 2001; pp. 197-209; vol. 44.
Tee, Oswald S., et al.; "The cleavage of aspirin by α- and β-cyclodextrins in basic aqueous solution;" *Can. J. Chem.*; 1985; pp. 3540-3544; vol. 63.
Vachon, M. G., et al.; "Physico-chemical evaluation of acetylsalicylic acid-Eudragit® RS100 microspheres prepared using a solvent-partition method;" *J. Microencapsulation*; 1995; pp. 287-305; vol. 12; No. 3.
Vachon, M. G., et al.; "The influence of microencapsulation using Eudragit® RS100 on the hydrolysis kinetics of acetylsalicylic acid;" *J. Microencapsulation*; 1997; pp. 281-301; vol. 14; No. 3.
Williams III, Robert O., et al.; "Influence of formulation technique for hydroxypropyl-β-cyclodextrin on the stability of aspirin in HFA 134a;" *European Journal of Pharmaceutics and Biopharmaceutics*; 1999; pp. 145-152; vol. 47.
Pandya, Shridhar J. et al.; "Compatible Polymer used as complexes in various drug delivery systems: β-Cyclodextrin;" *Pharmainfo.net Pharmaceutical Information, Articles and Blogs*; Mar. 1, 2008; vol. 6; issue 2 (12 pages).
Szejtli, Jozsef, Prof., Chem. Eng., PhD, DSc.; "Cyclodextrins in Drug Formulations: Part II;" *Pharmaceutical Technology*; Aug. 1991; pp. 24-26, p. 28, p. 34, p. 36, and p. 38.
Szejtli, Jozsef, Prof., Chem. Eng., PhD, DSc.; "Cyclodextrins in Drug Formulations: Part II;" *Pharmaceutical Technology*; Aug. 1991; pp. 24-38.
M. H. Lee et al.; "Freeze-thaw stabilization of sweet potato starch gel by polysaccharide gums;" *Food Hydrocolloids*; 2002; pp. 345-352; 16.

(56) References Cited

OTHER PUBLICATIONS

I.C.M. Dea et al.; "Synergistic Xanthan Gels", Chapter 13, pp. 174 to 182, of "*In Extracellular Microbial Polysaccharides*"; Sandford, P., et al.; ACS Symposium Series; American Chemical Society: Washington, DC, 1977.

Abraham G. White et al.; "Physiological and plharmacological regulation of human salivary electrolyte concentrations; with a discussion of electrolyte concentrations of some other exocrine secretions;" Medical Division, Montefiore Hospital New York and the Department of Medicine, The Mount Sinai Hospital, New York; 1954; pp. 246-255.

Dipjyoti Saha et al.; "Hydrocolloids as thickening and gelling agents in food: a critical review;" Journal of Food and Science Technology; 2010; pp. 587-597; vol. 47; No. 6.

Definition of "Therapeutic" from wwwthefreedictionary,com; 2013 Yes.

\* cited by examiner

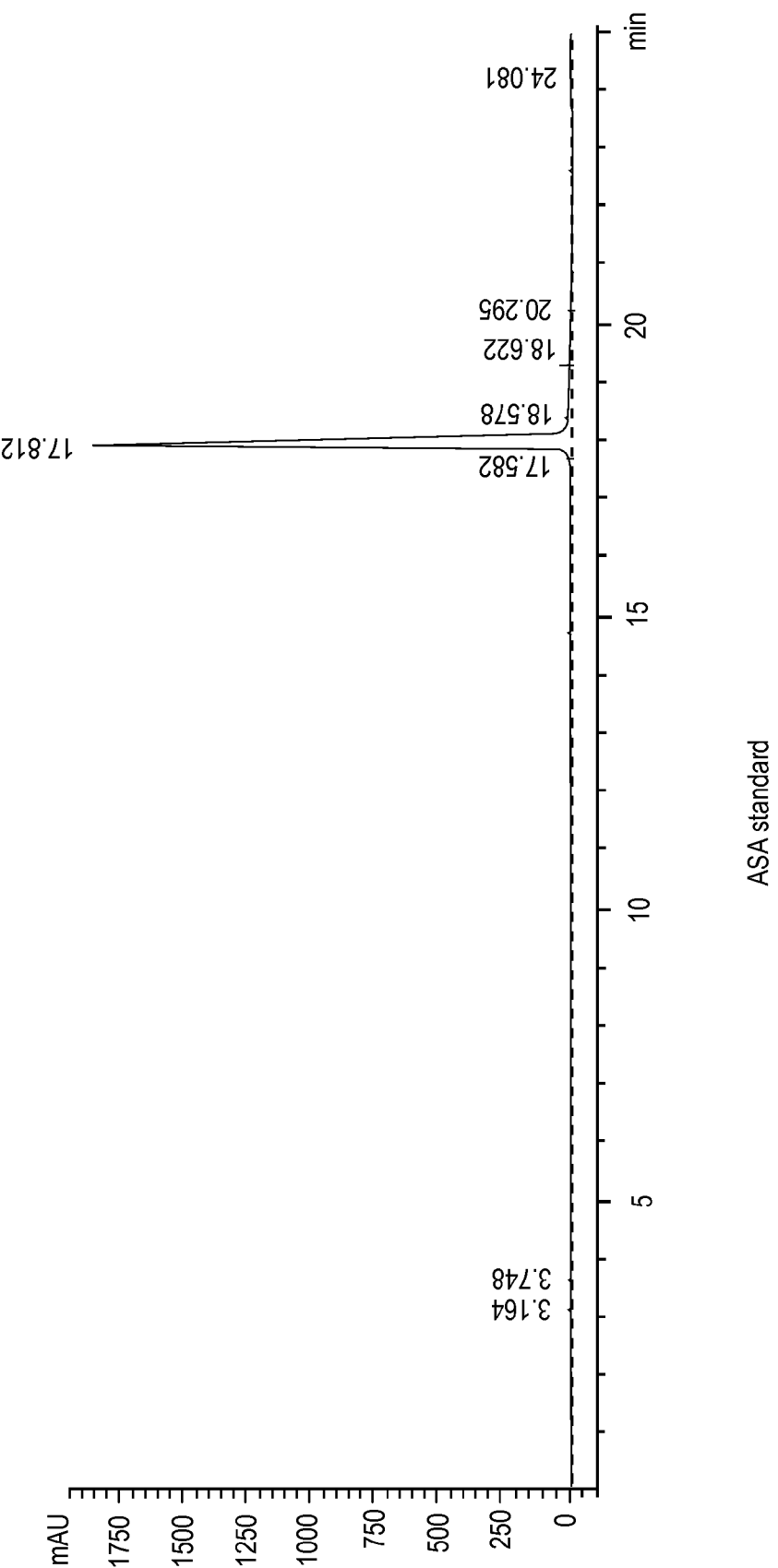
Figure 1. HPLC Chromatograms showing ASA stability after 40 days of 55° C storage in Gellan-βCD formulation

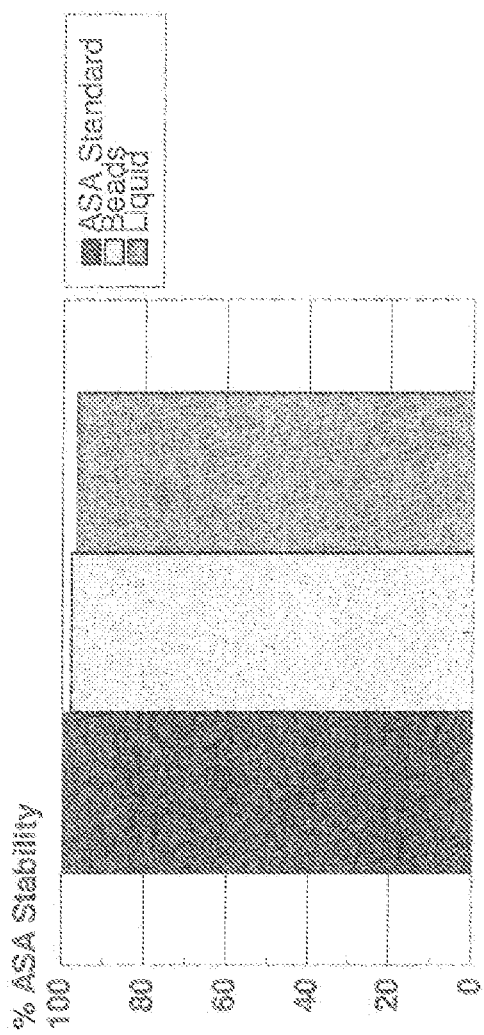
Figure 2. Stability of ASA in Gellan-βCD model system stored under accelerated storage conditions for 40 days at 35 °C (equivalent to approximately 18 months of storage using estimated storage time at 20 °C based on Q10 = 2).

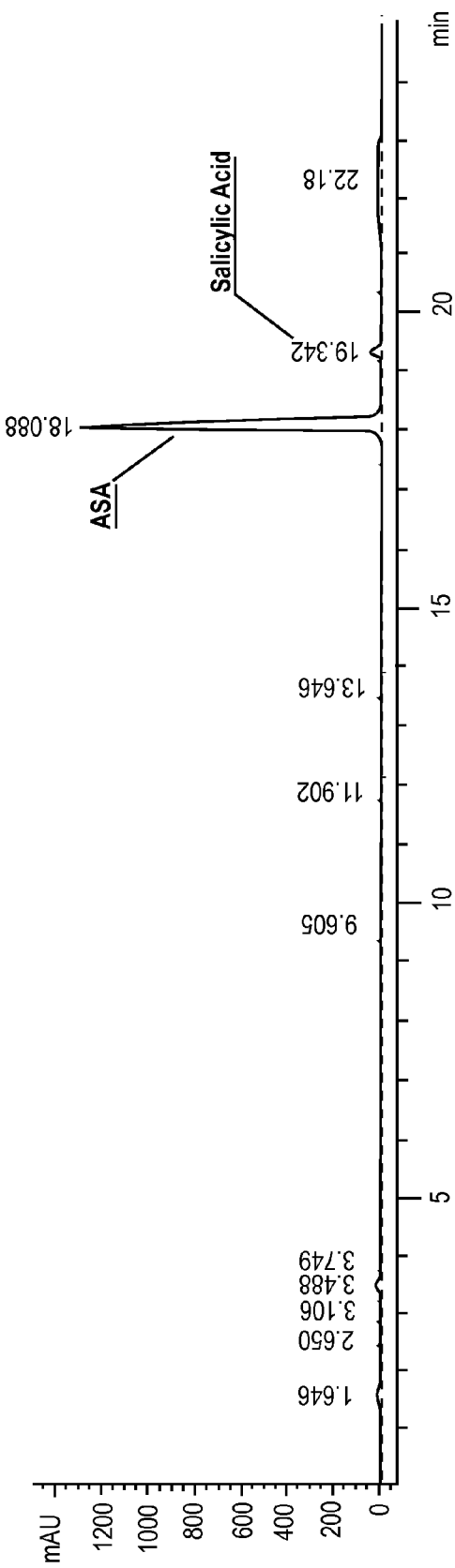
Figure 3. HPLC chromatogram of stable ASA in an alginate-βCD formulation (equivalent to 64 weeks at 20 C storage).

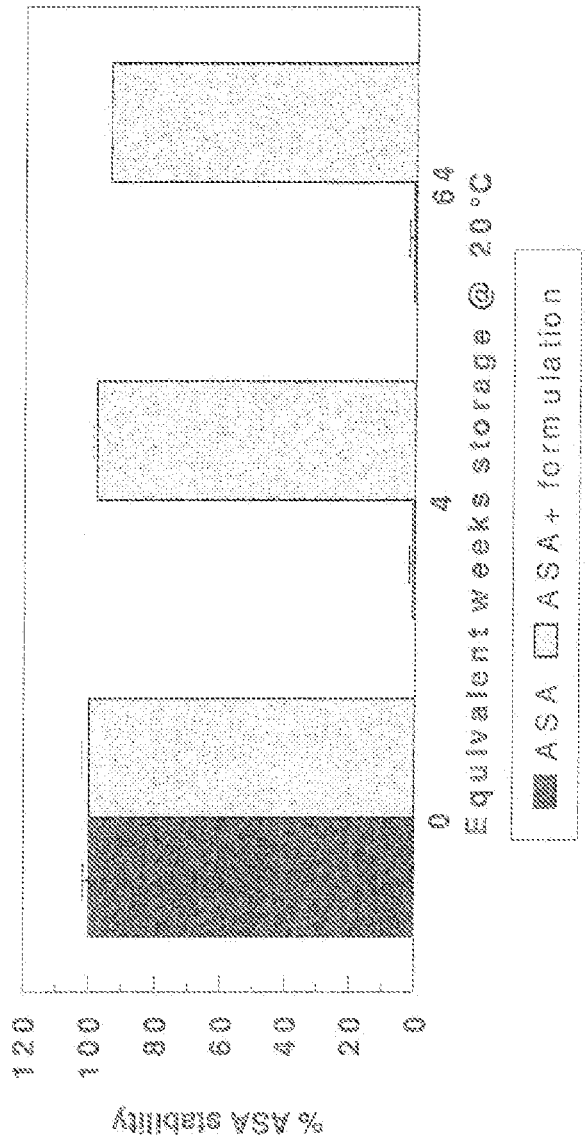
Figure 4. Stability of ASA in an alginate/βCD formulation vs ASA in water

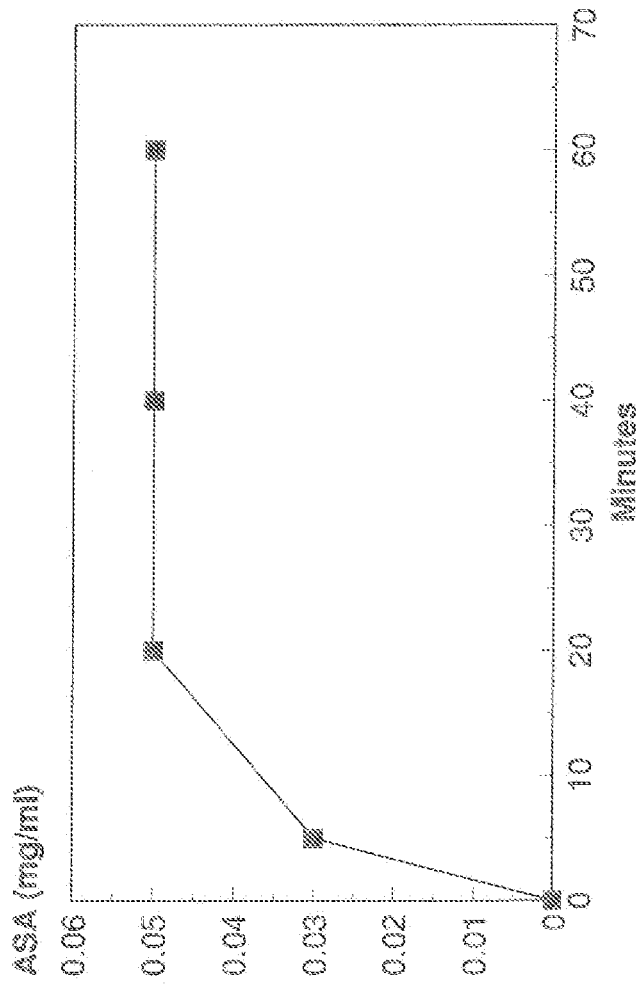
Figure 5 Chart depicting release of ASA from beads in Simulated Gastric Release Study

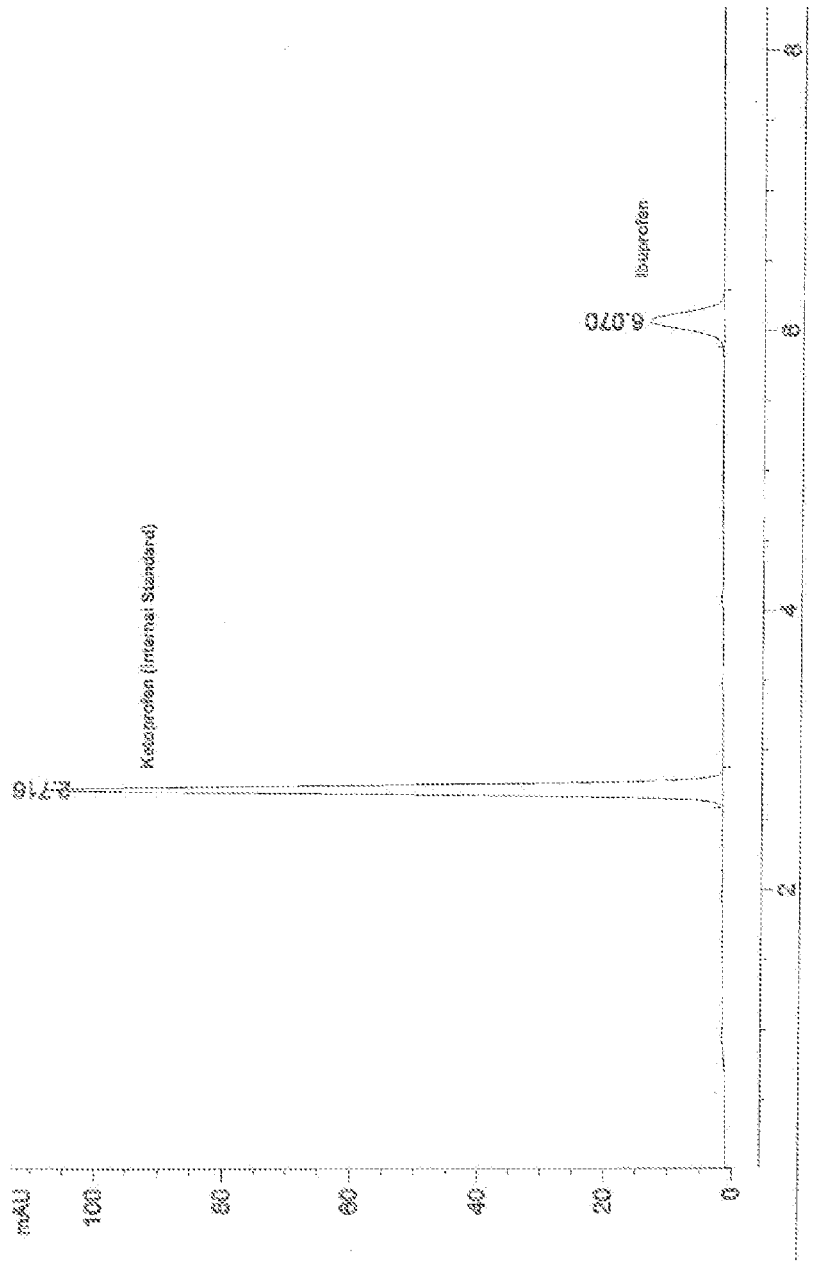
Figure 6a. HPLC Chromatograms showing Ibuprofen stability after 21 days of 55 °C storage in Gelluk-HPβCD formulation.

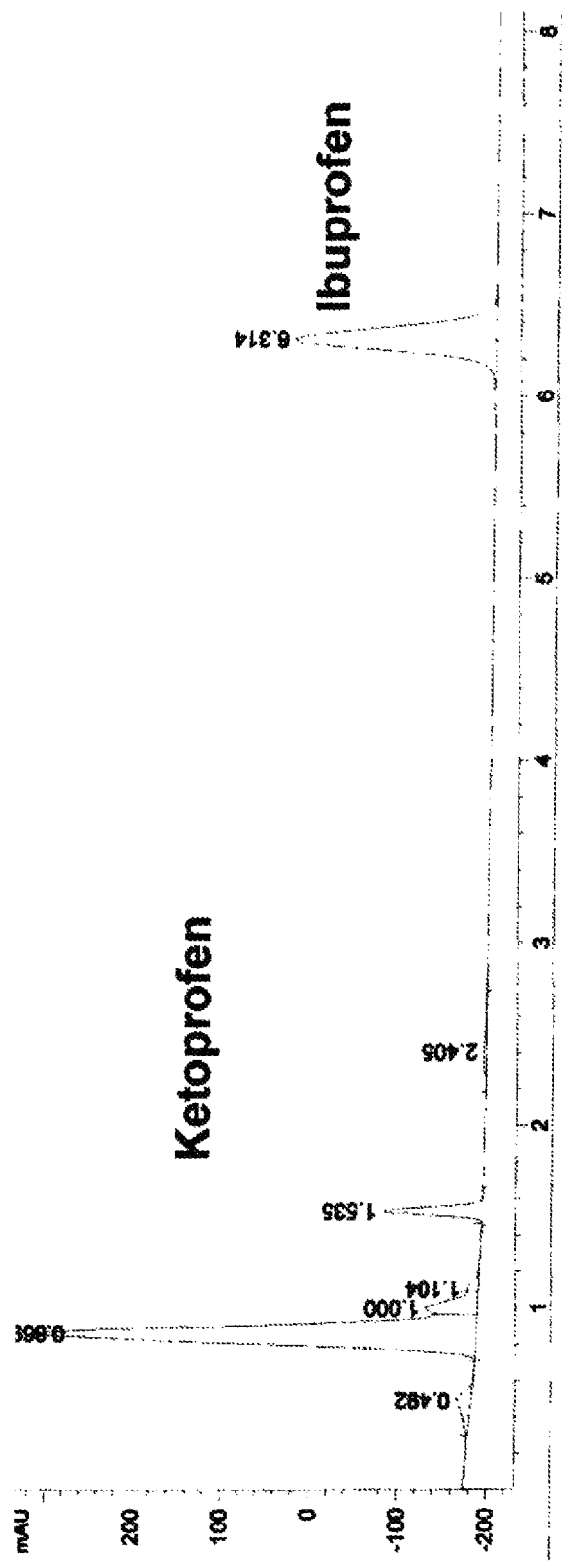
Figure 6a2- stable Ibuprofen within Gellan-HPβCD "bead portion" of prototype.

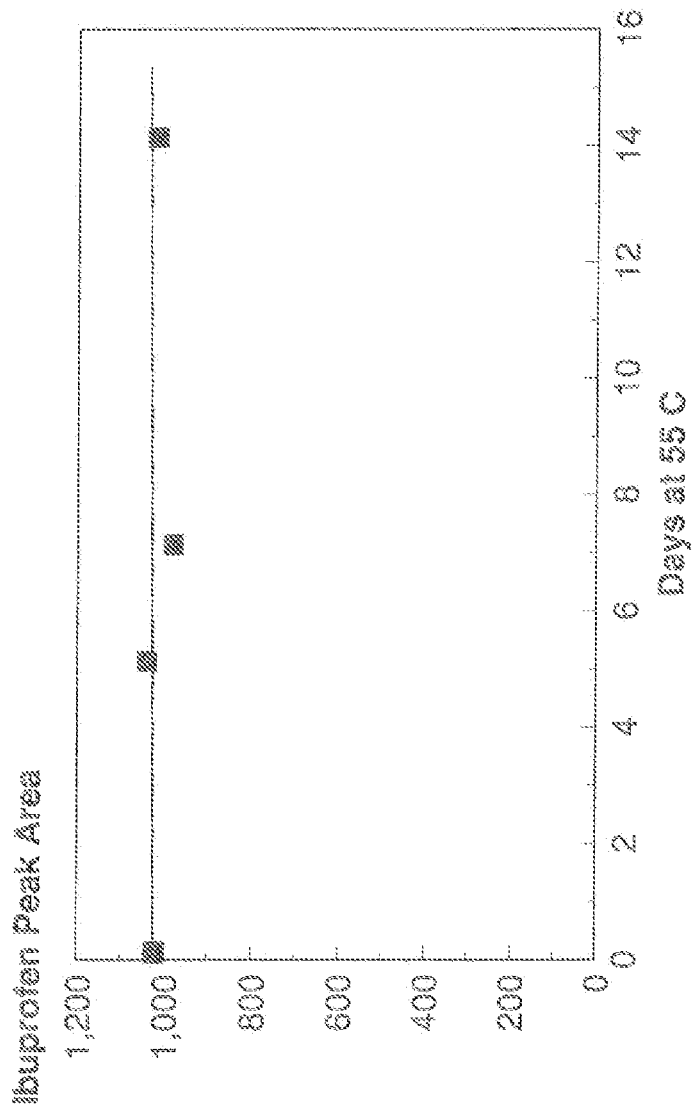
Figure 6b. Stability of Ibuprofen in Gellan-HPβCD model system stored under accelerated storage conditions.

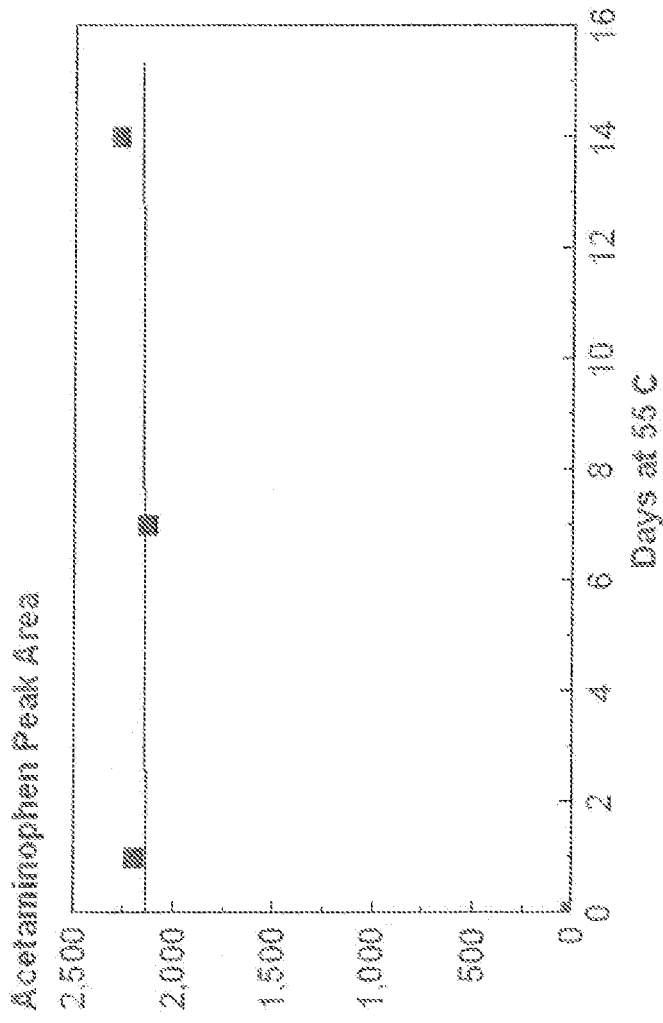
Figure 7. Stability of Acetaminophen in Gellan-HPβCD model system stored under accelerated storage conditions.

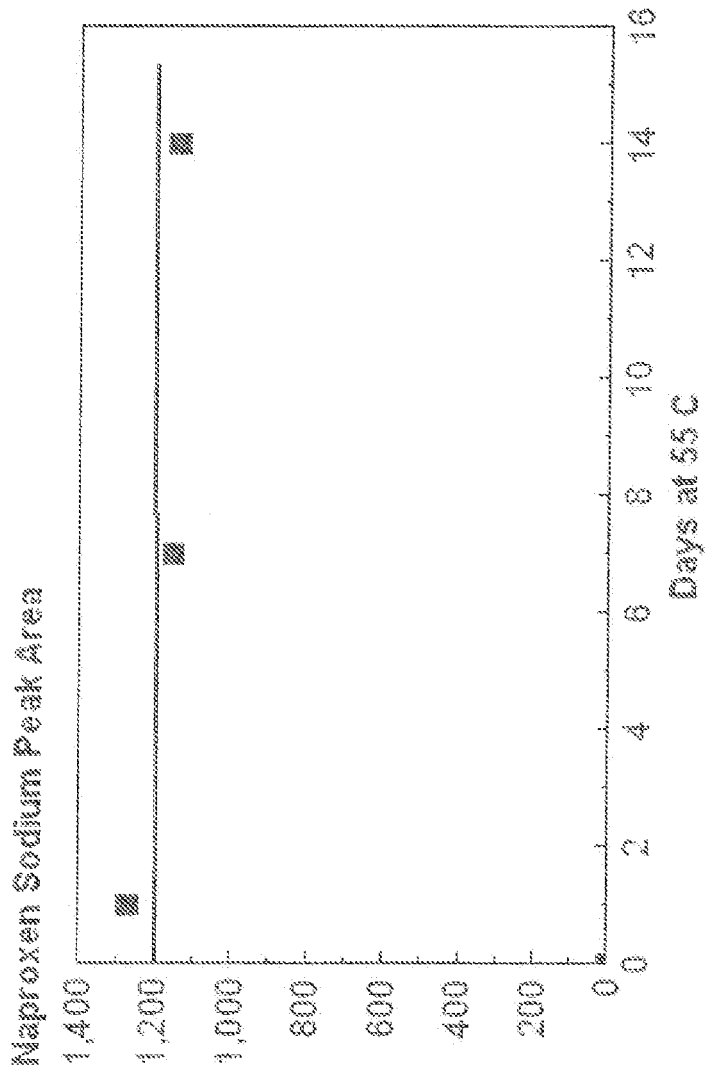
Figure 8. Stability of Naproxen Sodium in Gellan-HPβCD model system stored under accelerated storage conditions.

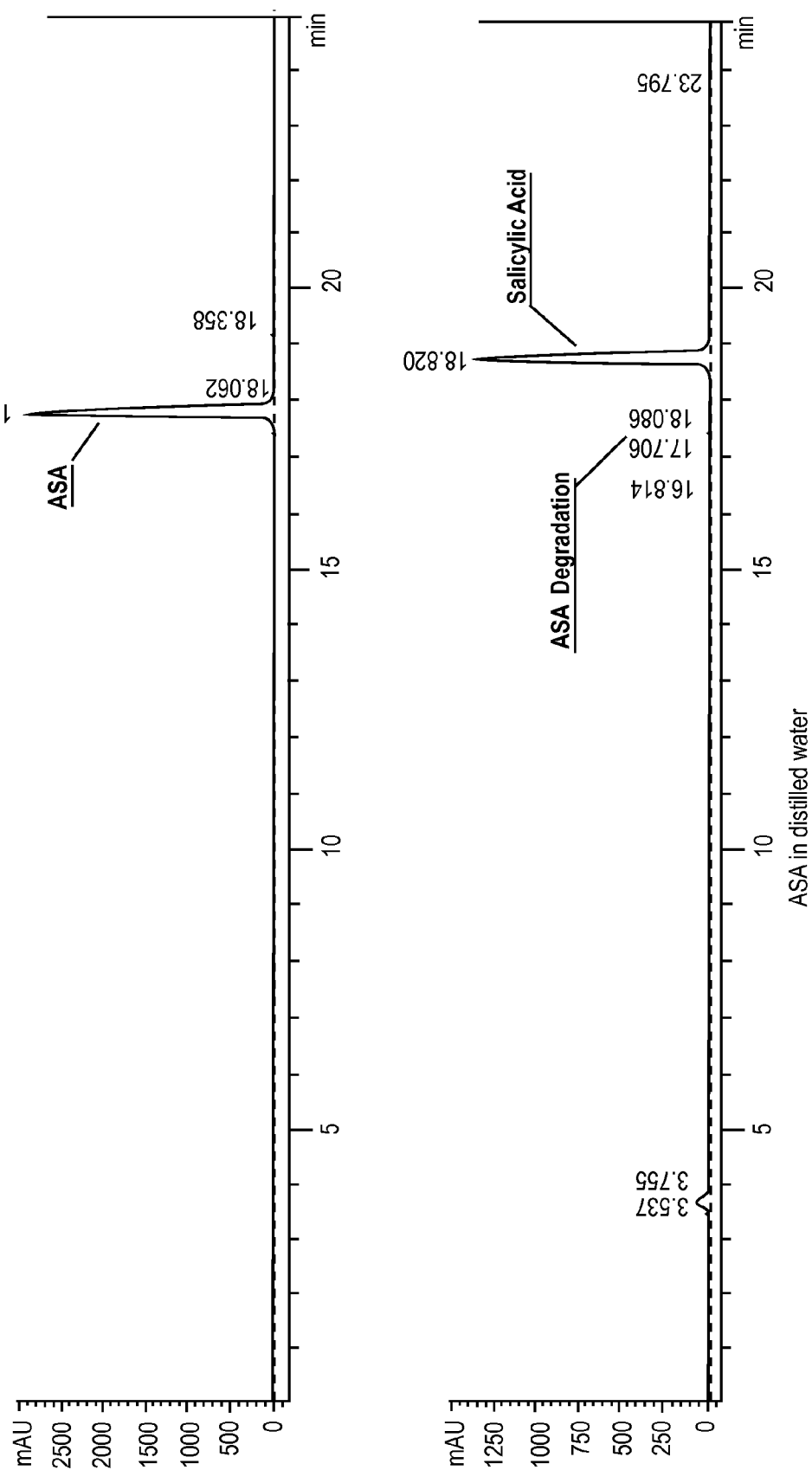
Figure 9. HPLC chromatogram showing ASA breakdown in distilled water after 3 weeks at 45 C.

AQUEOUS DRUG DELIVERY SYSTEM

CROSS REFERENCE TO RELATED APPLICATIONS

This application claims the benefit of U.S. Application No. 61/382,098, filed Sep. 13, 2010, the entirety of which is hereby incorporated herein by reference.

FIELD OF THE INVENTION

The present invention relates to water stable pharmaceutical compositions, their liquid dosage forms, and processes for their preparation. More particularly, this invention relates to pharmaceutical compositions comprising therapeutics, and their aqueous dosage forms, in the presence of an off-flavor masking agent and a water stable pharmaceutically acceptable matrix. Yet more particularly, this invention relates to pharmaceutical compositions comprising generally water-sensitive therapeutics, and their aqueous dosage forms, in the presence of an off-flavor masking agent and a water stable pharmaceutically acceptable matrix. Due in part to lowered reactivity of water-sensitive therapeutics in the pharmaceutical systems of the present invention when exposed to aqueous environments, these compositions may be used, inter alia, in liquid delivery systems of therapeutic agents.

BACKGROUND OF THE INVENTION

Drug products are currently designed for three groups of individuals: infants, pediatrics, and adults. The needs of infants are different from those of children 2 to 12 years of age, and the needs of children are different from those of adults. Moreover, the needs of the elderly population are different than those of other adults. Another category of individuals needing an alternative drug delivery form are patients with chronic dosage regimens. Repeated dosing of tablets or pills may become problematic for patients having a need for daily dosage regimens. Thus, an alternative dosage form is needed for a variety of patient populations.

Pediatric patients have difficulty swallowing until they reach the age of about 10-16 years old. Younger pediatric patients generally take either chewable tablets, crush and mix regular tablets with food/juice, or take a liquid dosage form. Chewable tablets, generally a good dosage form, do not always sufficiently mask the taste of the active agent. Crushing and mixing regular tablets with food or juice is time-consuming, messy, and not always practical. The difficulty of liquid dosage forms, e.g., syrups, is that they are bulky, do not always taste good, and can be unstable as compared to a solid dosage form, such as a tablet. A practical and new dosage form would be of value for these patients.

With advancements in medical science and the focus on healthy lifestyles, there is projected growth of the elderly population in the U.S. and abroad. Currently, the U.S. population of persons 65 years of age or older receives nearly 30% of the medications prescribed. Moreover, it is anticipated that there may be a rise in the demand for drugs by the elderly. In spite of the disproportionately large demand for prescription pharmaceuticals among the elderly, relatively little attention has been directed to meeting the unique pharmacotherapeutic needs of this age group.

Many older patients experience difficulty in swallowing tablets or capsules and yet the vast majority of dosage forms administered to the elderly are tablets or capsules. Uncoated tablets are convenient and economical to manufacture but are often difficult to swallow and frequently cause discomfort by "hanging" in the throat. Coated tablets and capsules are somewhat easier to swallow but with increasing age and the large number of drug products that are administered to a single individual, this is a source of apprehension. Liquid dosage forms are relatively easy to administer but are more costly, easily spilled, often do not taste good, occupy large volumes of space per dosage unit, and possess stability problems.

Relative to solid oral dosage forms, liquid formulations have the distinct advantages of dosage flexibility and ease of swallowing. A unit dosage equivalent to that of several capsules or tablets may be administered in as little as a single volume of liquid. Moreover, there is a recognized need for formulations to be available in a convenient, easy-to-take liquid dosage form. However, prior art formulations of liquid oral suspensions that provide chemical stability, and thus, commercially sufficient shelf life for water-sensitive therapeutic agents in aqueous formulations have met with only limited success to date. Commercially viable liquid products, especially aqueous liquid products, will need to maintain the stability of therapeutic agents present in liquid dispersal systems, provide comparable or improved release profiles from the dispersed phase at the point of the therapeutic agent's absorption, and limit free drug concentration in the dispersion medium.

The difficulties surrounding the formulation of water sensitive therapeutic agents are well known. Generally, the contacting of moisture or water adversely affects one or more chemical properties or functionality of the agent that are at least in part important to the agent's therapeutic efficacy. For example, aspirin (acetylsalicylic acid) is probably the most widely used drug in the world, but its sensitivity to water and concomitant ester hydrolysis has limited the manner in which aspirin may be administered to a patient. The hydrolysis of acetylsalicylic acid in the presence of water to salicylic acid and acetic acid occurs relatively quickly. Several other impurities form during hydrolysis have been reported including acetylsalicylic anhydride and acetylsalicylosalicylic acid. The decomposition of aspirin by water is said to result in a major loss of its pharmacological activity. This decomposition has tended to limit the marketing of acetylsalicylic acid to solid preparation forms, especially with regard to preparations useful for myocardial infarction prophylaxis. As a rule, solid aspirin preparations may only be administered orally with rapid decomposition/hydrolysis taking place primarily in the acidic environment of the stomach, during the absorption in the gastric mucuous membrane and the liver. It has been reported that oral administration leads to a situation where about half of the acetylsalicylic acid will reach the blood stream in its hydroyzed form (Burghart, U.S. Pat. No. 6,306,843). The hydrolysis product (salicylic acid) formed during aspirin's absorption by a patient is indicated as a contributor to side effects such as, e.g., gastric hemorrhage; and the overdosages required because of aspirin's rapid degradation during absorption constitute a considerable additional burden to patients.

Some researchers have attempted to stabilize water sensitive therapeutic compounds to hydrolysis. For example, Galat (U.S. Pat. No. 5,776,431) discloses certain solid compositions of aspirin in combination with certain alkaline compounds that are reportedly stable to hydrolysis as their powder forms as compared to other prior art solid compositions showing instability to water of hydration. Galat also reported that his solid compositions are soluble in water, but he failed to test or mention whether his compositions were stable in aqueous media over time.

Others have attempted to reduce hydrolysis in solid compositions by coating or encapsulating the therapeutic agents.

For example, Burgguiere et al. (U.S. Pat. No. 5,846,566) disclose certain coated aspirin particles wherein the coating agent consists of a coating composition comprising: at least one film-forming polymer insoluble in the gastrointestinal environment, at least one water-soluble polymer, at least one solid lubricating filler, and at least one hydrophobic plasticizer. Vachon and Nairn (J. Microencapsulation, 14(3), 281-301, 1997) describe the preparation of some aspirin microspheres prepared from certain acrylic polymers in non-aqueous solution as well as aspirin release from the microspheres over a 24 hour period.

Others have suggested the use of matrices for therapeutic agent delivery. For example, Malmsten (Soft Matter 2, 760-769, 2000) generally discloses the use of soft drug delivery systems including polymer and/or polysaccharide gels to provide patients with therapeutics.

Harel (US 2008/0044481) discloses certain microbeads containing oil-associated biologically active compounds and methods for their manufacture and use. The microbeads consist of a soluble complex of non-digestible polymer and emulsifier with oil-associated biologically active compounds embedded in a matrix of digestible polymer.

Agnihotri (European J. Pharmaceutics and Biopharmaceutics 63, 249-261 (2006)) studied the controlled release of cephalexin through gellan gum beads based on certain formulation parameters such as pH, therapeutic agent loading, in the presence of a particular mixture of calcium and zinc counterions.

Kedzierewicz et al.(Int. J. Pharmaceutics, 178, 129-136 1999) disclosed the preparation and release of a hydrophilic, water stable therapeutic agent, propranolol hydrochloride, from certain gellan gum beads.

McGurk et al. (U.S. Pat. No. 7,713,551) disclosed solid or semi-solid gelatin nanoparticulate active agent dosage forms comprising at least one nanoparticulate active agent composition and at least one gel forming substance which exhibits gelation sufficient to retain excess water in the solid or semi-solid gelatin form. The agent composition is said to require at least one active agent of certain particle size and at least one surface stabilizer adsorbed on or associated with the surface of the active agent. These dosage forms reportedly have the advantage of easy administration combined with rapid dissolution of the active agent following administration.

Attempts to eliminate hydrolysis of water sensitive therapeutic agents by merely employing non-aqueous liquids as delivery vehicles has met with limited success. For example, Burghart (U.S. Pat. No. 6,306,843) mentioned certain prior art stable acetylsalicylic acid solutions in pharmaceutically acceptable non-aqueous organic solvents such as e.g., propylene glycol, ethyl alcohol, glycerin or polyethylene glycol, that were prepared in an attempt to avoid hydrolysis of water sensitive compounds. He reported that even in these solvents, traces of moisture and accompanying de-esterification cannot be fully eliminated.

Hollenbeck (US 2006/0134148) discloses certain aqueous suspensions of drug delivery systems that comprise beads containing water soluble drugs that are coated with a material capable of controlling release of the highly soluble drug and immersed in an aqueous dispersion medium. In addition, products utilizing the Hollenbeck drug delivery systems reportedly have a long shelf life since the drug remains confined in the dispersed phase and any functional coatings remain intact. These compositions are said to comprise:

(a) a dispersed phase comprising an ion-exchange matrix drug complex comprising a pharmaceutically acceptable ion-exchange matrix and a water-soluble electrolytic drug associated with the ion-exchange matrix, wherein the surface charge of the ion-exchange matrix is opposite that of the electrolytic drug and a non-electrolytic, soluble, low molecular weight excipient; and (b) a dispersion medium.

Livney (2011/0038942) discloses certain colloidally stable dispersions of nanoparticles comprising beta-lactoglobulin and a polysaccharide which are transparent when diluted in aqueous media that are reportedly useful as, inter alia, delivery vehicles of hydrophobic nutraceuticals and fat-soluble vitamins.

Lee (US 2009/0104251) discloses reportedly heat stable microcapsule compositions that may include a protein, a polyanionic polymer, and a taste masking agent. Lee further discloses encapsulates that may include a protein and gellan gum.

Yokoyama, Hideakira et al (US 20050089577) disclose certain liquid matrices that reportedly undergo phase transfer in vivo and liquid oral preparations in which medicine can be easily solubilized, dispersed or suspended and swallowed. The liquid matrices are said to have favorable working properties in sterilization and a high stability because of their liquid nature. Yokoyama indicates that the matrices also exhibit an effect of masking bitterness, and gels in vivo so as to control the release speed of the medicine.

It would further be beneficial to achieve ease of administration with a drug delivery system exhibiting sufficient stability and/or bioavailability targeting young, older, and/or chronic dosage patients, especially those systems that are palatable to the targeted groups. Prior art gelatin dosage forms have been unable to solve this dual necessity of bioavailability in combination with active agent stability.

Previous liquid formulations, including for example, nanosol formulations may require a solvent to initially solubilize poorly soluble therapeutic agent in the matrix only to evaporate it subsequently. Alternatively the pH of of the matrix is adjusted to better dissolve the therapeutic. Such solubilization of an active agent is disclosed as undesirable, as solubilization may affect the various properties of the active agent, such as the solidification state of the active agent (i.e., whether the active agent is in an amorphous or crystalline form), stability of the active agent in the aqueous state, how much of the active agent has returned to the solid state, etc. See McGurk et al., U.S. Pat. No. 7,713,551. Moreover, solubilization of an active agent can change the active agent's pharmacological and pharmacokinetic characteristics.

Another drawback to certain of these formulation systems is that they does not retain excess water, which is essential for effective redispersability, and hence any dosage forms employing such formulations may exhibit poor pharmaceutical bioavailability. While the stability (e.g., water sensitivity) of therapeutic agents present in liquid dispersal systems, their release profiles from the dispersed phase, and their free drug concentration in the dispersion medium are all important for commercial success, their palatability to the consumer also factors into their degree of market acceptance. Therapeutic agents often carry a bitter taste profile that makes them unpalatable without masking. The bitter taste profile also can extend to a range of other pharmaceutical composition components, food and beverage ingredients and bulking agents, further complicating an agent's formulation. The desire for improved palatability in products including one or more of these moieties, especially in applications where the products are administered to pediatric patients, has prompted research efforts to reduce the impact of bitterness for end users. Overcoming bitter taste profiles in pharmaceuticals is especially problematic in liquid dose formulations. To be reasonably effective, the taste masking agent and therapeutic should preferably have similar physical properties, so that they act similarly with receptors and/or behave similarly in devised containment systems with regard to solubility and or leaching for example. Among common methods for achieving taste masking in solid oral compositions are included the use of flavor enhancers, polymer coatings, inclusion complex formation with cyclodextrin, use of ion exchange resins, solubility limiting methods, liposome, multiple emulsions, use of anesthetic agents, etc. See Ettner et al., "Reducing the Bitterness of Drugs," Pharmaceutical Formulation & Quality, September 2006.

Miyazaki et al. (Int. J. Pharmaceutics 297, 38-49 (2005) reported on the effect of certain polyhydric alcohol taste masking agents on in situ gelling pectin formulations for oral sustained delivery of acetaminophen and ambroxol. Pectin sols containing certain therapeutics reportedly gelled in situ in rat stomachs allowing assessment of bioavailability and sustained release of the therapeutic from the gel.

Prior art researchers have considered cyclodextrins for their potential to act as bitter taste masking agents in oral drug delivery. (See J. Szejtli et al., Euro. J. Pharmaceutics and Biopharmaceutics, 61, 115-125, 2005). In addition to taste masking ability, researchers have reported that cyclodextrins may help to improve drug bioavailability by increasing drug solubility, increase the rate of dissolution and stability of drug at its absorption site and/or in formulation, and/or reduce drug induced irritation (See, for example, Pandya, J., "Compatible Polymer used as Characterization Services Size complexes in various drug delivery systems," submitted Mar. 1, 2008 to Pharminfo.net.

Cyclodextrins are typically introduced in one of two ways into pharmaceutical compositions to assist in bitterness masking. In some instances preformed complexes or clathrates of therapeutics are employed in the compositions. However, Friesen stated that an inherent drawback of this approach is that incorporation of a pre-formed drug:cyclodextrin complex into a dosage form requires that the complex be prepared, isolated and purified. (See Friesen et al., US Patent Publication 2008/0075784). Alternatively, some therapeutics may be dry blended with cyclodextrins and added to the pharmaceutical composition as a physical mixture rather than a pre-formed complex. This approach can also have drawbacks. To demonstrate this point, some physical mixtures (e.g., dry blended) of unpleasant tasting drugs and cyclodextrin do not provide adequate taste masking. For example, a simple blend of cetirizine and beta-cyclodextrin reportedly still results in the bitter taste of cetirizine being tasted almost immediately. (See Friesen et al. US Patent Publication 2008/0075784).

Alternatively, Fanarra, US 2002/0032217 A1, discloses pre-forming (rather than blending the cyclodextrin and cetirizine) the drug:cyclodextrin complex and subsequently incorporating the pre-formed complex into dosage forms. Fanarra discloses forming solutions of cetirizine and beta-cyclodextrin that had reduced bitter taste due to the pre-formation of a drug:cyclodextrin complex.

While cyclodextrins have been used in pharmaceutical applications, Hladon reported an increase in the stability of an ibuprofen/beta-cyclodextrin complex at elevated temperature over time as compared to the non-complexed therapeutic agent (See Hladon et al. (J. Inclusion Phenomena and Macrocyclic Chemistry 36, 1-8, 2000)). Other reports have many compounds for which cyclodextrin complexation presents disadvantages which render them unsuitable for pharmaceutical use. See J. Szejtli, Pharmaceutical Technology, 1991, 24 38; and U.S. Pat. No. 5,362,860. Consequently, beneficial and/or adverse effects on multiple properties should be considered. For example, Tee and Takasaki (Can. J. Chem. 63, 3540-3544 1985) reviewed the stability of the water sensitive therapeutic, aspirin, when complexed with cyclodextrin and concluded that while the solubility of aspirin in aqueous solution may be enhanced through the use of the alpha-, and beta-cyclodextrin complexing agents, "any attempts to use these for pharmaceutical purposes should take into account the ability of cyclodextrins to promote the deacetylation of aspirin in aqueous solution." (See Tee and Takasaki at page 3540). Thus, in some situations, while one or more properties such as bioavailability may be improved through the use of cyclodextrin complexes alone, others such as shelf stability, efficacy, and/or the potential for increased side effects may be inadvertently adversely affected by the use of these same cyclodextrins.

It would be advantageous to provide water stable pharmaceutical compositions and liquid dosage forms derived therefrom employing therapeutic agents that minimize the effect of water on the therapeutic agents or their mode of action. This is especially true for water sensitive therapeutic agents, where hydrolysis, especially during shelf storage, and in particular in aqueous drug delivery systems, may lead to the production of by-products that reduce overall efficacy and/or increase side effects.

Additionally, there is a need for water stable pharmaceutical compositions and shelf stable aqueous liquid dosage forms derived therefrom that are not only easier to orally ingest than tablets for patients but are palatable to the taste. In certain areas of the world where water quality limits the ability to provide such water sensitive therapeutic agents in aqueous solution, it may be useful to further provide compositions and/or liquid dosage forms of these agents that may be safely ingested. As such, the ability to prepare these therapeutic compositions in the appropriate dosages in advance at locations far removed, where water quality in not an issue, would facilitate treatment of those affected by certain diseases, disorders, or conditions. It remains a challenge to achieve pharmaceutically acceptable suspension liquid dosage forms containing a pharmaceutically active ingredient in the dispersed phase, having a low free drug concentration in the dispersion medium, and capable of providing immediate or sustained drug release from the dispersed phase after administration to a patient. Improvements that would allow manufacturers to provide pre-formed drug:cyclodextrin complexes into a dosage form without the necessity that the complex be isolated and purified are also desirable. The present invention is directed to these and other important ends.

SUMMARY OF THE INVENTION

Accordingly, the present invention is directed, in part, to water stable pharmaceutical compositions comprising a therapeutic agent; and an off-flavor masking agent; in a pharmaceutically acceptable matrix.

In other embodiments, the present invention is directed to liquid form oral pharmaceutical compositions comprising a water stable pharmaceutical composition, and a pharmaceutically acceptable aqueous liquid medium, wherein said water stable pharmaceutical composition comprises a therapeutic agent and an off-flavor masking agent in a pharmaceutically acceptable matrix.

In still other embodiments, the present invention is directed to processes for preparing a water stable pharmaceutical composition comprising a therapeutic agent; and an off-flavor masking agent; in a water stable pharmaceutically acceptable matrix, preferably gel matrix, said process comprising contacting the therapeutic agent, the off-flavor masking agent, and a pharmaceutically acceptable matrix precursor, preferably gel matrix precursor, in an aqueous medium, for a time and under conditions effective to provide a water stable pharmaceutical composition in a pharmaceutically acceptable matrix, preferably gel matrix.

In some embodiments, the present invention is directed to kits, comprising:

a. a liquid form oral pharmaceutical composition in one or more containers; and b. instructions for administering the liquid form oral pharmaceutical composition;

wherein:

the liquid form oral pharmaceutical composition comprises a water stable pharmaceutical composition, and a pharmaceutically acceptable aqueous liquid medium, wherein the water stable pharmaceutical composition comprises a therapeutic agent and an off-flavor masking agent in a pharmaceutically acceptable matrix.

In some embodiments, the present invention is directed to rehydration beverage compositions, comprising:

a water stable pharmaceutical composition;

optionally mineral or non-mineral nutritional supplements; and a pharmaceutically acceptable aqueous liquid medium;

wherein said water stable pharmaceutical composition comprises a therapeutic agent and an off-flavor masking agent in a water stable pharmaceutically acceptable matrix; and wherein the aqueous liquid medium comprises an isotonic solution.

In some embodiments, the present invention is directed to methods of prophylaxis and/or treatment of a disease, disorder, condition, or symptoms thereof, comprising administering to a patient in need thereof a liquid form oral pharmaceutical composition comprising a water stable pharmaceutical composition, and a pharmaceutically acceptable aqueous liquid medium, wherein said water stable pharmaceutical composition comprises a therapeutic agent and an off-flavor masking agent in a pharmaceutically acceptable matrix. In certain preferred embodiments, the present invention is directed, in part, to such methods of prophylaxis and/or treatment as disclosed throughout this disclosure, wherein the acceptable aqueous liquid medium is an isotonic liquid and may optionally further comprise mineral or non-mineral nutritional supplements.

In other embodiments, the present invention is directed to liquid form oral pharmaceutical compositions having commercially acceptable shelf life, as such shelf life is understood by the ordinarily skilled artisan.

In certain embodiments, the invention is directed to water stable pharmaceutical compositions and their liquid form oral pharmaceutical compositions, kits, and rehydration beverage compositions containing such water stable compositions, wherein the compositions and kits are heat stable, and as such may be exposed to, for example, retort processing at about 121° C. and about 15 PSI for about 60 minutes, or hot fill pasteurization at about 104° C.

The foregoing and other objectives, features, and advantages of the invention will be more readily understood upon consideration of the following detailed description of the invention.

BRIEF DESCRIPTION OF THE DRAWINGS

FIG. 2 shows a graph comparing the stability of ASA in a gellan/βCD formulation of the present invention to that of ASA in water.

FIG. 3 is an HPLC chromatogram depicting the stability of ASA in an alginate formulation containing ASA (equivalent to 64 weeks at 20° C. storage).

FIG. 4 shows a graph providing the stability of ASA in a Gellan-βCD composition of the present invention system stored under accelerated storage conditions for 40 days at 55° C.

FIG. 5 show a graph depicting the release of ASA from a βCD/gellan bead composition of the present invention in a Simulated Gastric Release Study.

FIG. 6a show HPLC Chromatogram showing ibuprofen stability after 21 days of 55° C. storage in Gellan-HPβCD formulation. The initial chromatogram is an analysis of an ketoprofen internal standard and ibuprofen standard; the middle chromatogram gives an analytical indication of the stability of ibuprofen within the Gellan-HPβCD "bead portion" of the present invention.

FIG. 6b is a graph showing the stability of ibuprofen in a Gellan-HPβCD composition of the present invention stored under accelerated storage conditions.

FIG. 7 is a graph showing the stability of acetaminophen in a Gellan-HPβCD composition of the present invention stored under accelerated storage conditions.

FIG. 8 is a graph showing the stability of naproxen sodium in a Gellan-HPβCD composition of the present invention stored under accelerated storage conditions.

DETAILED DESCRIPTION OF ILLUSTRATIVE EMBODIMENTS

Figure 1:
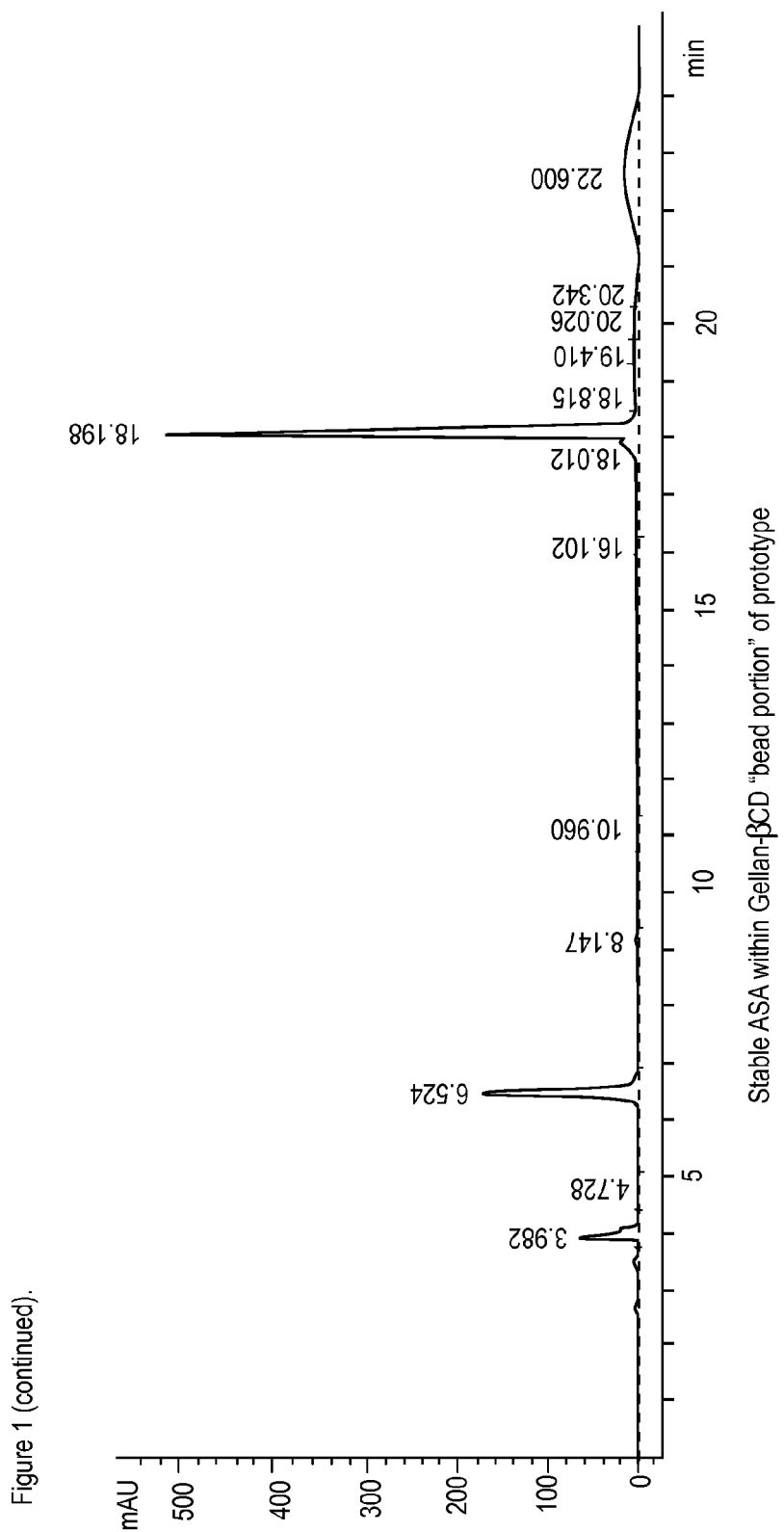
FIG. 1 depicts three HPLC Chromatograms showing ASA stability after 40 days of 55° C. storage in Gellan-βCD formulation. The initial chromatogram is an analysis of an ASA standard; the middle chromatogram gives an analytical indication of the stability of ASA within the Gellan-βCD "bead portion" of the present invention; the latter chromatogram is an analysis of contained ASA in the aqueous delivery vehicle at the end of the stability study.
Figure 1:
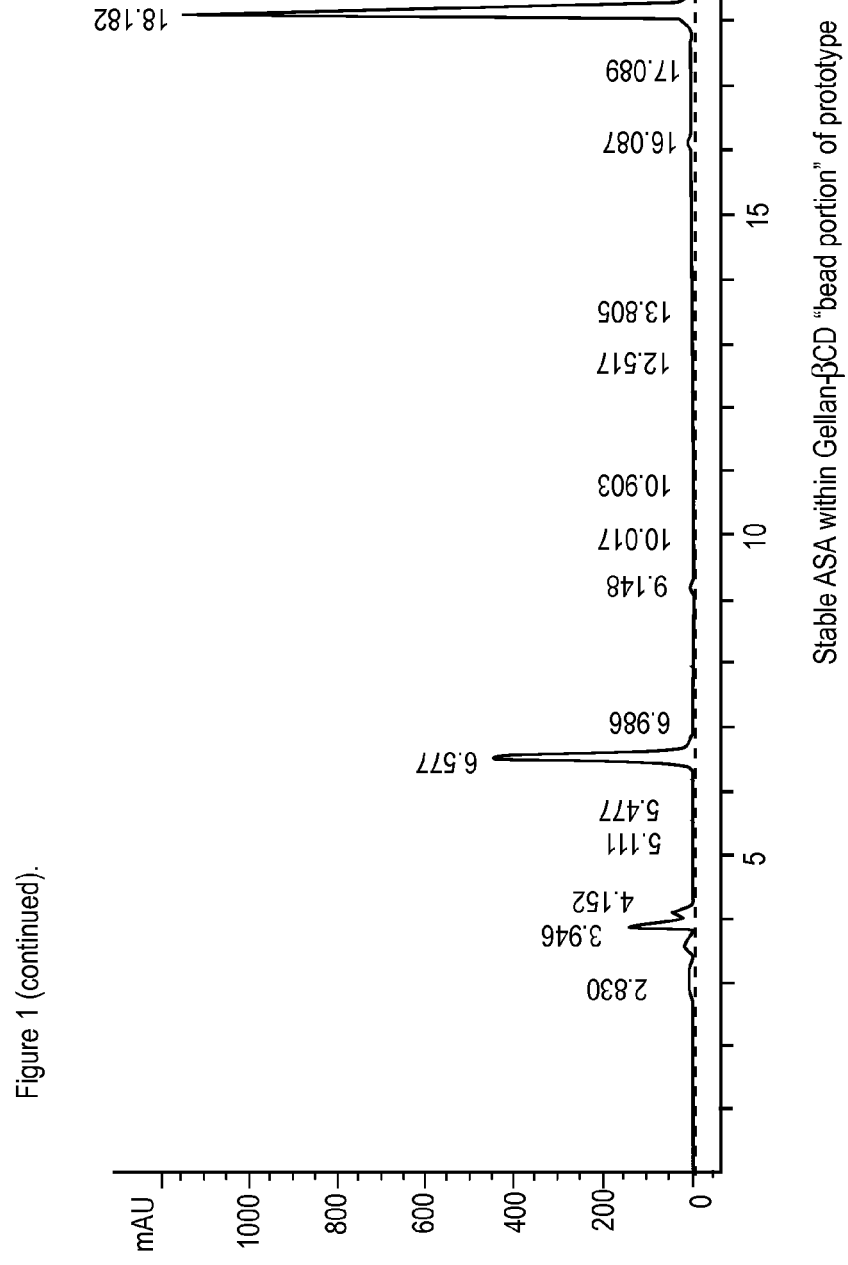

As employed above and throughout the disclosure of the present invention, the following terms, unless otherwise indicated, shall be understood to have the following meanings.

As used herein, the term "water stable" refers to the ability of a compound, agent, matrix, or composition, in the presence of water, to retain substantially all of the necessary therapeutic, chemical and/or physical properties that were associated with said compound, agent, matrix, or composition prior to its contact with water. With regard to retaining necessary properties, "substantially all" refers to at least about 75%, preferably 80, more preferably 85, still more preferably 90, yet more preferably 95, even more preferably 97, with at least about 99% of those necessary properties associated with the compound, agent, matrix, or composition prior to its contact with water. For example, a water stable pharmaceutical composition refers to a pharmaceutical composition wherein the integrity of the chemical and/or physical properties, and thus the effectiveness associated with one or more of the water stable pharmaceutical composition's components, especially those of the therapeutic agent, is substantially retained after the composition's contact with an aqueous solution for use in delivering the pharmaceutical composition.

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein, the term "water sensitive" refers to the ability of water, in physical contact over a period of time with a compound, agent, or composition, or functionality within the compound, agent, or composition, to alter at least one chemical or therapeutic property or functionality. For example, acetyl salicylic acid (aspirin) is a water sensitive therapeutic agent whose acetyl group is susceptible to reaction with water over a period of time, said time dependent on the conditions, such as the temperature to which the water and compound (e.g., aspirin), agent or composition are exposed. Over a period of time, aspirin is converted to salicylic acid by contacting with water. The therapeutic and/or chemical properties of acetylsalicylic acid are known to be different than those of the water-reaction product salicyclic acid and/or acetic acid. Thus aspirin can be said to be water sensitive because its contacting with water over time modifies one or more of the therapeutic and/or chemical properties of the aspirin.

As used herein, the term "heat stable composition" refers to a composition wherein substantially all of the therapeutic agent remains in the matrix, preferably gel matrix of the water stable pharmaceutical compositions, and wherein the integrity of the chemical and/or physical properties, and thus the effectiveness associated with one or more of the water stable pharmaceutical composition's components, especially those of the therapeutic agent, is substantially retained after the composition's contact with heat under retort or hot fill pasteurization conditions. Gellan matrices are described on the web as heat stable under UHT and HTST processing conditions. See *Kelcogel Gellan Gum Book*, 5$^{th}$ Ed., June 2007.

As used herein, the term "commercially acceptable shelf life" refers to the ability of a commercial product comprising a composition of the present invention to remain stable to substantial degradation of active therapeutic agent for a period of at least about 6 months under typical shelf storage conditions (about 20° C.), preferably at least about 9 months, more preferably at least about 12 months. Compositions were typically exposed to oven storage temperatures of 55° C. and samples routinely taken to ascertain a threshold level of stability for acetylsalicylic acid over time. A general discussion of shelf life and related analytical procedures is found in the article "*Food Product Shelf Life*" by Mark Sewald and Jon De Vries of Medallions Laboratories, Minneapolis, Minn., including sections on the kinetics of shelf-life testing and the concept of $Q_{10}$. Procedures described therein using a $Q_{10}$ of 2 were used to estimate shelf storage stability under more typical shelf storage conditions (20° C.).

As used herein, the term "gel" refers to a three dimensional hydrophyllic network having chemical or physical cross-links, said networks capable of imbibing large amounts of water or aqueous biological fluids. Gels, as defined herein, are hydrated and thus contain some amount of water incorporated within them. Non-limiting examples of the numerous macromolecules capable of gel formation include polysaccharides, such as for example, alginate, carrageenan, destran, gellan, gura gum, hyaluronic acid, pullulan, schleroglucan, xanthan, xyloglucan, pectins, chitosan, and the like. "Gel precursors" or "gelling agents" typically refer to the same macromolecules, albeit in the absence of water or prior to hydration.

These gel precursors preferably form gels in the presence of water and either certain ions or a variation in the pH of the aqueous solution.

As used herein, the term "ion specific gel" refers to any gelling agent that is capable of gel formation initiated by divalent cations, and/or gellation reversal in the presence of monovalent cations. Non-limiting examples include alginate, chitosan, pectins, and derivatives thereof.

As used herein, the term "non ion specific gel" refers to any gelling agent that is capable of gel formation initiated by monovalent or divalent cations or combination thereof. Non-limiting examples include gellan, and derivatives thereof.

As used herein, the term "cyclic oligosaccharide" refers to a compound formed by the joining of about 5 to about 10 saccharide residues arranged into a ring in which an enclosed tubular space allows reception of a guest molecule to form a clathrate.

As used herein, the term "cyclodextrin" refers to a cyclic oligoglucoside containing about 5 to about 10 glucose residues in which an enclosed tubular space allows reception of a guest molecule to form a clathrate. Typical examples include alpha-, beta-, and/or gamma-cyclodextrin, or their derivatives, or mixtures thereof.

As used herein, the term "therapeutic agent:cyclodextrin complex" refers to a physical association between the therapeutic agent and the cyclodextrin; preferably this takes the form of a clathrate-type complex, wherein the therapeutic agent acts as the guest molecule in the enclosed tubular space of the cyclodextrin host.

As used herein, the term "at least a portion", when taken in the context of an amount of therapeutic agent or off-flavor masking agent refers independently to at least about 5% by weight of the therapeutic agent and/or off-flavor masking agent respectively, preferably, about 10%, more preferably about 15%, still more preferably about 20%, with at least about 25% by weight based on the total weight of the therapeutic agent and/or off-flavor masking agent being even more preferred.

As used herein, the term "a substantial portion" refers to at least about 30% of the therapeutic agent employed in the present methods and/or compositions complexes with the cyclodextrin, preferably, about 35%, more preferably about 40%, with at least about 45% by weight based on the total weight of the of the therapeutic agent employed being even more preferred.

As used herein, the term "substantially all" means that more than about 50% by weight of the therapeutic agent employed in the present methods complexes with the cyclodextrin, preferably more than about 60% by weight, more preferably more than about 75% by weight, even more preferably more than about 90% by weight, still more preferably more than about 95% by weight, and most preferably more than about 99% by weight of the compound complexes with the cyclodextrin. When used in conjunction with water contained within an aqueous liquid medium, the term "substantially all" means that more than about 50% by volume of the aqueous medium employed in the present methods is water, preferably more than about 60% by volume, more preferably more than about 75% by volume, even more preferably more than about 90% by volume, still more preferably more than about 95% by volume, and most preferably more than about 99% by volume of the aqueous medium is water.

As used herein, the term "liquid oral dosage form" refers to a dosage form wherein the therapeutic agent is contained, preferably suspended, within a pharmaceutically acceptable aqueous medium.

As used herein, the term "aqueous medium" and "aqueous liquid medium" each refer to a liquid medium comprising a substantial amount of water on a per unit volume liquid medium basis. Preferably, the aqueous medium is substantially all water, as defined herein.

Therapeutic agents should be understood to include the neutral form of the drug and pharmaceutically acceptable forms thereof. "Pharmaceutically acceptable" refers to those compounds, materials, compositions, salts and/or dosage forms which, within the scope of sound medical judgment, are suitable for administration to patients without excessive toxicity, irritation, allergic response, or other problems or complications commensurate with a reasonable benefit/risk ratio. By "pharmaceutically acceptable forms" thereof is meant any pharmaceutically acceptable derivative or variation, including stereoisomers, stereoisomer mixtures, enantiomers, solvates, hydrates, isomorphs, polymorphs, pseudomorphs, salt forms and prodrugs. Preferably in some embodiments, the pharmaceutically acceptable forms include salt forms. In other preferable embodiments the pharmaceutically acceptable forms include, any stereoisomer or stereoisomeric mixture of the therapeutic agent.

As used herein, the term "limited solubility in water" refers to a therapeutic agent dissolving to an extent of less than about 0.5 grams of therapeutic agent per mL of water at 25° C., preferably less than about 0.2 g, more preferably less than about 0.1 g, still more preferably less than about 0.05 g, yet more preferably less than about 0.02 g, with less than about 0.01 g per mL of water being even more preferred.

"Side effect" refers to a consequence other than the one(s) for which a therapeutic agent is used, for example, the adverse effects produced by a drug, especially on a tissue or organ system other than the one sought to be benefited by its administration. In the case, for example, of aspirin, the term "side effect" refers, inter alia, to such conditions as gastric irritation, inflammation, heartburn, nausea and pain.

"Dosage unit" refers to physically discrete units suited as unitary dosages for the particular individual to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

As used herein, the terms "preservative system" or "preservatives" include all preservatives approved for use in food and beverage compositions including, without limitation, such known chemical preservatives as benzoates including sodium, calcium, and potassium benzoate, sorbates including sodium, calcium, and potassium sorbate, citrates including sodium citrate and potassium citrate, polyphosphates including sodium hexametaphosphate (SHMP), and mixtures thereof, and antioxidants such as ascorbic acid, EDTA, BHA, BHT, TBHQ, dehydroacetic acid, dimethyldicarbonate, ethoxyquin, heptylparaben, and combinations thereof. Preservatives can be used in amounts not exceeding mandated maximum levels.

As used herein, the term "fruit flavor" refers to those flavors derived from the edible reproductive part of a seed plant, especially one having a sweet pulp associated with the seed. Also included within the term "fruit flavor" are synthetically prepared flavors made to simulate fruit flavors derived from natural sources. Non-limiting examples of fruit flavors include the citrus flavors orange, lemon, lime, and grapefruit, and such flavors as apple, grape, cherry, and pineapple flavors and the like, or a mixture thereof.

As used herein, the term "botanical flavor" refers to flavors derived from parts of a plant other than the fruit. As such, botanical flavors can include those flavors derived from essential oils and extracts of nuts, bark, roots and leaves. Also included within the term "botanical flavor" are synthetically prepared flavors made to simulate botanical flavors derived from natural sources. Examples of such flavors include cola flavors, tea flavors, and the like, and mixtures thereof.

This invention is directed to, inter alia, the surprising and unexpected discovery of new water stable pharmaceutical compositions that may be administered to a patient in an aqueous liquid delivery vehicle. Prior to the present invention, while gel dosage forms were desirable for a number of reasons, there was an inherent conflict between desiring more water in the dosage form to increase redispersion of the active agent, and knowing that the presence of a significant percentage of water can result in degradation of the active agent to be delivered. Thus, shelf stability of the therapeutic agent could be seriously compromised in prior art systems where water was introduced to facilitate the agent's redispersion. It was unexpectedly discovered that the presence of water does not destabilize or degrade the therapeutic agents in the dosage forms of the present invention.

Benefits of the compositions, and/or dosage forms containing such compositions of the invention and/or kits containing such compositions of the invention can include, but are not limited to: (1) rapid delivery of the active agent, which can correlate with rapid therapeutic agent absorption; (2) stability of the active agent, which can include chemical stability of the active agent; (3) excellent redispersability of the active agent upon administration or in a biorelevant media; (4) similar or improved bioavailability of the active agent as compared to a microparticulate or solubilized form of the same active agent, administered at the same dosage; (5) a more consistent bioavailability profile for the active agent, aiding in dosage determination, due to the more consistent active agent particle sizes present in the gelatin dosage form, as compared to a microparticulate or solubilized form of the same active agent, administered at the same dosage; (6) easy administration, requiring only swallowing of small amounts of and aqueous delivery vehicle containing the composition; (7) substantially reduced perceptions of any unpleasant taste of a therapeutic agent; (8) the dosage form particularly useful for infant, pediatric, and elderly patient populations, as well as other patient populations which have difficulty in swallowing pills or other solid dosage forms; (9) better patient compliance as the dosage form is easier to consume and digest as compared to conventional solid dose forms, such as tablets; (10) improved protection of water sensitive therapeutic agents; and (11) improved shelf life storage of dosage forms comprising the compositions in an aqueous delivery vehicle.

Accordingly, in certain embodiments, the present invention provides water stable pharmaceutical compositions comprising:
 a therapeutic agent; and
 an off-flavor masking agent;
 in a pharmaceutically acceptable matrix, as well as methods for preparing said water stable pharmaceutical compositions.

In certain preferred embodiments of the present invention, the water stable pharmaceutical compositions are substantially stable in the presence of the aqueous liquid medium for at least about 20 days at 55° C. (equivalent to approximately 240 days at 20° C.) using a $Q_{10}$ of 2 for the estimation). Preferably the water stable pharmaceutical compositions are substantially stable in the presence of the aqueous liquid medium for at least about 25 days at 55° C. (equivalent to approximately 300 days at 20° C. using a $Q_{10}$ of 2), more preferably for at least about 30 days at 55° C. (equivalent to approximately 360 days at 20° C. using a $Q_{10}$ of 2), with at least about 40 days at 55° C. (equivalent to approximately 480 days at 20° C. using a $Q_{10}$ of 2) being even more preferred. As used herein, the term "substantially stable" refers to those embodiments of water stable pharmaceutical compositions wherein the therapeutic agent retains substantially all of the necessary therapeutic, chemical and/or physical properties that were associated with said therapeutic agent prior to its contact with water, such as for example, the water that comprises the aqueous liquid medium, wherein the term "substantially all" is as herein defined.

In some preferred embodiments of the present invention, the water stable pharmaceutical compositions are provided in a liquid oral dosage form, preferably in a unit liquid oral dosage form.

In certain preferred embodiments, the water stable pharmaceutical compositions, liquid form oral pharmaceutical compositions, kits, and rehydration beverage compositions of the present invention have excellent heat stability properties (i.e., they are heat stable to typical processing conditions). Preferably, the compositions help reduce or prevent breaking of the matrix when heated in an aqueous system. In other preferred embodiments, the water stable pharmaceutical compositions, liquid form oral pharmaceutical compositions, kits, and rehydration beverage compositions of the present invention possess stability and structural integrity for at least about 60 minutes in retort processing at about 121° C. and about 15 PSI or hot fill pasteurization at about 104° C. In other words, when the water stable pharmaceutical compositions are exposed to retort processing at about 121° C. and about 15 PSI for about 60 minutes or hot fill pasteurization at about 104° C., substantially all of the therapeutic agent, off-flavor masking agent or complex or combination thereof remains in the matrix of the water stable pharmaceutical composition.

Alternatively, the chemical and/or physical properties of any water sensitive therapeutic agent are substantially unaffected by the aqueous system into which it is placed and exposed to such retort processing or hot fill pasteurization conditions. Retort processing is described for example, in 21 C.F.R. Section 113 (thermally processed low-acid foods packaged in hermetically sealed containers). Hot fill pasteurization is described in 21 C.F.R. Section. 114 (acidified foods) and 21 C.F.R. Section. 131 (milk and cream). In this manner, the water stable pharmaceutical composition also provides protection for therapeutic agents, such as aspirin, that are sensitive to hydrolysis in the presence of an aqueous liquid medium, In even more preferred embodiments, the compositions are heat stable and provide protection for water sensitive therapeutic agents.

In other preferred embodiments, the water stable pharmaceutical compositions, liquid form oral pharmaceutical compositions, kits, and rehydration beverage compositions of the present invention are stable to UHT (around 1-2 seconds at a temperature exceeding about 135° C.) or HTST pasteurization (composition is heated to about 72° C. for at least about 15 seconds) processing conditions.

In certain embodiments, the water stable pharmaceutical compositions, liquid form oral pharmaceutical compositions, kits and and/or beverage compositions of the present invention overcome drawbacks associated with the prior art by expanding the range of therapeutic agents that may be provided to a mammalian host in liquid form oral pharmaceutical compositions, more preferably aqueous liquid form oral pharmaceutical compositions to include those that heretofore could not be effectively employed due to water sensitivity and/or ineffective taste masking.

In some preferred embodiments, the water stable pharmaceutical compositions of the present invention contain less than a substantial amount of beta-lactoglobulin, and preferably contain not more than a de minimis quantity of beta-lactoglobulin, with containing no beta-lactoglobulin being more preferred.

In some other preferred embodiments, the water stable pharmaceutical compositions of the present invention contain less than a substantial amount of a polyoxyethylene-polyoxypropylene triblock copolymer of general formula E106 P70 E106, preferably contain not more than 15% by weight of the water stable composition, more preferably not more that 5% by weight, still more preferably not more than a de minimis quantity of a polyoxyethylene-polyoxypropylene triblock copolymer of general formula E106 P70 E106, with containing no a polyoxyethylene-polyoxypropylene triblock copolymer of general formula E106 P70 E106 being more preferred.

In other preferred embodiments, the therapeutic agent contained in the water stable pharmaceutical compositions and/or liquid form oral pharmaceutical compositions is substantially released in the gastrointestinal tract, more preferably substantially all of the therapeutic agent from the composition is released in the gastrointestinal tract.

In certain preferred embodiments, the present invention provides water stable pharmaceutical compositions and/or liquid form oral pharmaceutical compositions wherein the matrix comprises a gel, more preferably a non-ion-specific gel; yet more preferably comprising a non-ion-specific gel comprising a polysaccharide; with a non-ion-specific gel comprising gellan being even more preferred.

In certain other preferred embodiments a gel moiety shape retention compound, preferably xanthan gum, may be added to the composition. Typically, this compound is optionally added to the composition before, during, or subsequent to addition of gel matrix precursor, preferably gellan, but prior to setting the gel during preparation of the water stable pharmaceutical compositions of the present invention to assist in shape retention, preferably bead shape retention, of the gel matrix once it is set. Other non-limiting examples of gel moiety shape retention compounds include locust bean gum and guar gum.

The invention is also directed in part to water stable pharmaceutical compositions, liquid form oral pharmaceutical compositions, kits, and rehydration beverage compositions comprising off flavor taste masking agents. Off flavor masking agents may be employed to reduce the adverse flavor impact from the pharmaceutically acceptable matrix or one or more of the therapeutic agents contained therein. Non-limiting examples of off-flavor taste masking agents useful in pharmaceutical applications include for example sweeteners such as aspartame, compressible sugar, dextrates, lactose, mannitol, sucrose, maltose, sodium saccharin, sorbitol, and xylitol, nanolipidic particles, cyclic oligosaccharides, and flavors. Preferably, the off-flavor taste masking agent is not chemically bonded to the pharmaceutically acceptable matrix.

Examples of flavors that may be useful as off flavor masking agents include, but are not limited to, food grade flavors. The food grade flavors may be synthetic or artificial flavors, natural flavors or any mixture thereof. Examples of suitable flavors include, but are not limited to, almond, amaretto, apple, green apple, apple-cherry-berry, apple-honey, apricot, bacon, balls of fire, banana, barbeque, bay, beef, roast beef, beef steak, berry, berry blue, birch beer/spruce beer, black-berry, bloody mary, blueberry, boysenberry, brandy, bubble gum, butter, butter pecan, buttermilk, butterscotch, candy corn, cantaloupe, cantaloupe lime, caramel, carrot, cassia, caviar, celery, cereal, champagne, cherry, cherry cola, cherry maraschino, wild cherry, black cherry, red cherry, cherry-cola, chicken, chocolate, chocolate almond, cinnamon spice, citrus, citrus blend, citrus-strawberry, clam, cocoa, coconut, toasted coconut, coffee, coffee almond, cola, cola-vanilla, cookies & cream, cool, cotton candy, cranberry, cranberry-raspberry, cream, cream soda, dairy type cream, creme de menthe, cucumber, black currant, dulce de leche, egg nog, pork fat, type fat, anchovy fish, herring fish, sardine fish, frankfurter, fiery hot, fried garlic, sauteed garlic, gin, ginger ale, ginger beer, graham cracker type, grape, grape grapefruit, grapefruit-lemon, grapefruit-lime, grenadine, grill, guarana, guava, hazelnut, honey, hot, roasted honey, ice cream cone, jalapeno, key lime, kiwi, kiwi-banana, kiwi-lemon-lime, kiwi-strawberry, kola champagne, lard type, lemon, lemon custard, lemonade, pink lemonade, lemon-lime, lime, malt, malted milk, mango, mango-pineapple, maple, margarita, marshmallow, meat type, condensed milk, cooked milk, mint, mirepoix, mocha, mochacinna, molasses, mushroom, sauteed mushroom, muskmelon, nectarine, neopolitan, green onion, sauteed onion, orange, orange cordial, orange creamsicle, orange creme, orange peach mango, orange strawberry banana, creamy orange, mandarin orange, orange-passion-guava, orange-pineapple, papaya, passion fruit, peach, peach-mango, peanut, roasted peanut, pear, pecan danish type, pecan praline, pepper, peppermint, pimento, pina colada, pina colada/pineapple-coconut, pineapple, pineapple-orange, pistachio, pizza, pomegranate, pork fat type, baked potato, prune, punch, citrus punch, tropical punch, cherry fruit punch, grape punch, raspberry, black raspberry, blue raspberry, red raspberry, raspberry-blackberry, raspberry-ginger ale, raspberry-lime, roast type, root beer, rum, sangria, sarsaparilla, sassafras, sausage, sausage pizza, savory, seafood, shrimp, hickory smoke, mesquite smoke, sour, sour cream, sour cream and onion, spearmint, spicy, strawberry, strawberry margarita, jam type strawberry, strawberry-kiwi, burnt sugar, sweet, supersweet, sweet & sour, tallow, tamarind, tangerine-lime, tangerine, tea, tequila type, thyme, toffee, triple sec, tropical fruit mix, turkey, tutti frutti, vanilla, vanilla cream, vanilla custard, french vanilla, vegetable, vermouth, vinegar, balsamic vinegar, watermelon, whiskey, wildberry, wine, winter green, and yogurt. Other examples of flavors are found in 21 C.F.R. §§172.510, 172.515, 172.520, 172.530, 172.535, 172.575, 172.580 and 172.585, which are hereby fully incorporated by reference. A variety of food grade flavors are commercially available from, for example, Sensient Flavors Inc., Indianapolis, Ind., Givaudan SA, Cincinnati, Ohio, and International Flavors & Fragrances, New York, N.Y.

In other preferred embodiments the present invention provides water stable pharmaceutical compositions and/or liquid form oral pharmaceutical compositions wherein the off-flavor masking agent comprises a cyclic oligosaccharide; more preferably wherein the cyclic oligosaccharide contains from about 5 to about 10 monosaccharide units; still more preferably wherein the cyclic oligosaccharide is a cyclodextrin or derivative or mixture of cyclodextrins or derivatives thereof; yet more preferably wherein the cyclodextrin comprises alpha-, beta-, or gamma-cyclodextrin, or a derivative or mixture thereof; with a cyclodextrin comprising alpha-cyclodextrin or beta-cyclodextrin, or a derivative or mixture thereof being even more preferred. In certain even more preferred embodiments, the cyclic oligosaccharide is a cyclodextrin comprising alpha-cyclodextrin or a derivative thereof. Alternatively, in other even more preferred embodiments, the cyclic oligosaccharide is a cyclodextrin comprising beta-cyclodextrin, or a derivative thereof.

Examples of cyclodextrins useful in the present invention include alpha-, beta-, or gamma-cyclodextrins and/or alkyl and hydroxyalkyl derivatives thereof, with beta-cyclodextrin and derivatives of beta-cyclodextrin, in certain embodiments being the most preferred from, inter alia, the standpoint of availability and cost or alpha-cyclodextrin and derivatives of alpha-cyclodextrin, in certain embodiments being the most preferred from, inter alia, the standpoint of allowable consumption levels as presently permitted by the FDA.

Exemplary derivatives of cyclodextrins include mono- or polyalkylated alpha- or beta-cyclodextrin, mono- or polyhydroxyalkylated alpha- or beta-cyclodextrin, mono-, tetra-, or hepta-substituted alpha- or beta-cyclodextrin, and sulfoalkyl ether cyclodextrin (SAE-CD). Specific cyclodextrin derivatives for use herein include hydroxypropyl-beta-cyclodextrin, hydroxyethyl-beta-cyclodextrin, hydroxypropyl-gamma-cyclodextrin, hydroxyethyl-gamma-cyclodextrin, dihydroxypropyl-beta-cyclodextrin, glucosyl-alpha-cyclodextrin, glucosyl-beta-cyclodextrin, diglucosyl-beta-cyclodextrin, maltosyl-alpha-cyclodextrin, maltosyl-beta-cyclodextrin, maltosyl-gamma-cyclodextrin, maltotriosyl-beta-cyclodextrin, maltotriosyl-gamma-cyclodextrin, dimaltosyl-beta-cyclodextrin, methyl-beta-cyclodextrin, sulfobutyl ether cyclodextrin (SBE-CD), and mixtures thereof such as maltosyl-beta-cyclodextrin, or idimaltosyl-beta-cyclodextrin. In some embodiments, the preferred cyclodextrin is beta-cyclodextrin. In other embodiments the preferred cyclodextrin is alpha-cyclodextrin.

Generally speaking cyclic oligosaccharides, preferably cyclodextrins, play the role of host molecules, and easily form inclusion complexes with a wide variety of guest molecules. The only requirement for successful inclusion is that the guest molecule must fit at least partially into the cyclic oligosaccharide cavity. Each cyclic oligosaccharide has its cavity and thus the size of the guest it can accommodate therein, defined by, inter alia, the number of monosaccharides that together form the ring. Therefore, the ordinarily skilled artisan is capable of choosing one or more cyclic oligosaccharides as candidates to inclusion complexes with guest molecules (such as the therapeutic agents employed in the present invention) based on the known internal dimensions of the contained cavity and the three dimensional shape of the desired guest molecule.

Typically the cavity or pocket of the cyclic oligosaccharide is more hydrophobic than the exterior portion. Consequently, Guest molecules such as therapeutic agents that have more hydrophobic character tend to incorporate more readily into the cyclic oligosaccharide cavity.

Benefits gained by complexation of guest compounds with cyclic oligosaccharide, preferably cyclodextrins, include altering the solubility of the guest compound, stabilizing against adverse light effects and/or degradation from heat and oxidation, masking of unwanted physiological effects, and reducing volatility. The cyclic oligosaccharide can partially shield the drug molecule from attack by various reactive molecules (such as water, in some embodiments of the present invention).

In certain embodiments of water stable pharmaceutical compositions of the present invention, at least a portion of the cyclodextrin and at least a portion of the therapeutic agent are present in the pharmaceutical composition as a therapeutic agent:cyclodextrin complex, more preferably wherein a substantial portion of the therapeutic agent is complexed with the cyclodextrin, still more preferably wherein substantially all of the therapeutic agent is complexed with the cyclodextrin.

In certain other preferred embodiments, the present invention provides water stable pharmaceutical compositions and/or liquid form oral pharmaceutical compositions wherein the therapeutic agent is selected from water-sensitive therapeutic agents, more preferably from the group consisting of aspirin, naproxen sodium, acetaminophen, and ibuprofen. In other preferred embodiments, the present invention provides water stable pharmaceutical compositions and/or liquid form oral pharmaceutical compositions wherein the therapeutic agent is ibandronate sodium.

The invention is directed, in part, to water stable pharmaceutical compositions, liquid form oral pharmaceutical compositions, kits, and rehydration beverage compositions comprising an unpleasant tasting and/or water sensitive therapeutic agent capable of being administered orally that has some degree of solubility in water. Preferably, the therapeutic agent has limited solubility in water. The invention finds particularly desirable application in pharmaceutical compositions wherein the therapeutic agent is unpleasant tasting and/or is water sensitive. The invention also finds utility in certain instances where drugs only slowly dissolve in water and/or have low taste thresholds; i.e., drugs that may be detected by their taste at low dissolved drug concentrations. Alternatively preferred are those therapeutic agents found in over-the-counter products. Also alternatively preferred are any therapeutic agents useful within the myriad of OTC drugs that are presently found in pill, tablet, or capsule form, or in alcohol-based syrups. The indications associated with these over-the counter therapeutic agents include but are not limited to any cough, cold, and/or flu medications, any types of sinus, antihistamine, and/or allergy medications, specific or general pain treatment medications, pediatric beverage medications, anti-gas, upset stomach, and diarrhea formulations, anti-cholesterol formulations, such as those containing phytosterols and phytostenols, and/or anti-smoking formulations containing nicotine.

Exemplary therapeutic agents capable of oral administration that may be used with the current invention include, without limitation, inorganic and organic compounds that act on the peripheral nerves, adrenergic receptors, cholinergic receptors, nervous system, skeletal muscles, cardiovascular smooth muscles, blood circulatory system, synaptic sites, neuroeffector junctional sites, endocrine and hormone systems, immunological system, reproductive system, autocoid systems, alimentary and excretary systems, inhibitors of autocoids and histamine systems. Preferred classes of therapeutic agents include, but are not limited to, antacids, analgesics, anti-anginals, anti-anxiety agents, anti-arrhythmics, anti-bacterials, antibiotics, anti-diarrheals, anti-depressants, anti-epileptics, anti-fungals, anti-histamines, anti-hypertensives, anti-inflammatory agents, anti-virals, cardiac agents, contraceptives, cough suppressants, cytotoxics, decongestants, diuretics, drugs for genito-urinary disorders, drugs for use in parkinsonism and related disorders, drugs for use in rheumatic disorders, hypnotics, minerals and vitamins, lipid lowering drugs and sex hormones. Veterinary drugs may also be suitable for use with the present invention. In certain preferred embodiments, the therapeutic agent is other than a nucleoside or nucleotide.

Specific examples of unpleasant-tasting therapeutic agents include acetaminophen, albuterol, aminoguanidine hydrochloride, aminophylline, amitriptyline, amoxicillin trihydrate, ampicillin, amlodipine besylate, aspirin, azithromycin, barbiturates, berberine chloride, caffeine, calcium carbonate, calcium pantothenate, cephalosporins, cetirizine, chloramphenicol, chlordiazepoxide, chloroquine, chlorpheniramine, chlorpromazine, cimetidine, ciprofloxacin, clarithromycin, codeine, demerol, dextromethorphan, digitoxin, digoxin, diltiazem hydrochloride, diphenhydramine, diphenylhydantoin, doxazosin mesylate, doxylamine succinate, eletriptan, enoxacin, epinephrine, erythromycin, ethylefrine hydrochloride, etinidine, famotidine, fluconazole, glipizide, gualfenesin, ibuprofen, indeloxazine hydrochloride, lidocaine, lomotil, loratadine, lupitidine, magnesium oxide, meclizine, methacholine, morphine, naproxen, neostigmine, nifentidine, niperotidine, nizatidine, ofloxacin, paracetamol, pefloxacin, penicillin, phenobarbital, phenothiazine, phenylbutazone, phenylpropanolamine, pipemidic acid, pirbuterol hydrochloride, piroxicam, prednisolone, propranolol hydrochloride, pseudoephedrine, pyridonecarboxylic acid antibacterials, ranitidine, roxatidine, salicylic acid, sertaraline hydrochloride, sildenafil, spironolactone, sulbactam sodium, sulfonamides, sulfotidine, sulpyrine, sultamicillin tosylate, tenidap, terfenadine, theophylline, trimethoprim, tuvatidine, valdecoxib, zaltidine, and zonisamide. Another non-limiting example is ibandronate sodium.

Therapeutic agents employed in the methods and compositions of the present invention may exist in prodrug form. As used herein, "prodrug" is intended to include any covalently bonded carriers which release the active parent therapeutic agent employed in the present methods and compositions in vivo when such prodrug is administered to a mammalian subject. The term "prodrug" also includes therapeutic agents specifically designed to maximize the amount of active species that reaches the desired site of reaction which are of themselves typically inactive or minimally active for the activity desired, but through biotransformation are converted into biologically active metabolites. Since prodrugs are known to enhance numerous desirable qualities of pharmaceuticals (e.g., solubility, bioavailability, manufacturing, etc.) the therapeutic agents employed in the present composition and/or methods may, if desired, be delivered in prodrug form. Thus, the present invention contemplates compositions of prodrugs and delivery methods thereof. Prodrugs of the therapeutic agents employed in the present invention may be prepared by modifying functional groups present in the compound in such a way that the modifications are cleaved, either in routine manipulation or in vivo, to the parent compound.

Accordingly, prodrugs include, for example, therapeutic agents described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

In other embodiments, the present invention is directed to liquid form oral pharmaceutical compositions comprising a water stable pharmaceutical composition, and a pharmaceutically acceptable aqueous liquid medium, said water stable pharmaceutical composition comprising a therapeutic agent and an off-flavor masking agent in a pharmaceutically acceptable matrix; as well as methods for preparing said liquid form oral pharmaceutical compositions. In certain preferred embodiments, the pharmaceutically acceptable matrix, preferably gel matrix, said matrix containing the therapeutic agent and the off-flavor masking agent, forms a discontinuous phase in the liquid form oral pharmaceutical composition, wherein the discontinuous phase is more preferably provided in the form of gel beads. While beads are typically rounded or spheroidal in shape, this shape is normally a consequence of processing a matrix into a gel. In accordance with the present invention, the shape and/or size of the gel moiety is not critical so long as the gel moiety does not substantially interfere with the therapeutic action or adversely affect the desired properties of the water stable pharmaceutical compositions, liquid form oral pharmaceutical compositions, kits, and rehydration beverage compositions.

In certain preferred embodiments, the liquid form oral pharmaceutical compositions are provided in kit form.

In other embodiments, the invention is directed to kits, comprising:

a. a container comprising a liquid form oral pharmaceutical composition of the present invention as described hereinabove; and b. instructions for administering the liquid form oral pharmaceutical composition.

In certain preferred embodiments, the liquid form oral pharmaceutical composition in the kit container provides an individual dose of therapeutic agent.

Pharmaceutical kits useful in, for example, the treatment of pain, which comprise a therapeutically effective amount of a therapeutic agent indicated for the treatment of pain in a water stable pharmaceutical composition, liquid form oral pharmaceutical composition, or beverage of the present invention, in one or more sterile containers, are also within the ambit of the present invention. Sterilization of the container may be carried out using conventional sterilization methodology well known to those skilled in the art. The sterile containers of materials may comprise separate containers, or one or more multi-part containers, as exemplified by the UNIVIAL™ two-part container (available from Abbott Labs, Chicago, Ill.), as desired. Multiple doses of the water stable pharmaceutical composition, liquid form oral pharmaceutical composition, or beverage composition of the present invention may be separately packaged in unit dosage form, or combined into a single package form. Instructions, either as inserts or as labels, indicating quantities of the components to be administered, guidelines for administration, and/or guidelines for mixing the components, may also be included in the kit.

In yet other embodiments, the water stable pharmaceutical compositions are provided in combination with vitamins, minerals, amino acids, sweeteners, flavors, and/or preservatives in the form of an isotonic, rehydration, or supplemental nutrient beverage composition. In certain preferred embodiments of such isotonic, rehydration, or supplemental nutrient beverage compositions containing the water stable pharmaceutical compositions of the present invention, the water stable pharmaceutical composition's pharmaceutically acceptable matrix, preferably gel matrix, said matrix containing the therapeutic agent and the off-flavor masking agent, forms a discontinuous phase in the liquid form oral pharmaceutical composition, wherein the discontinuous phase is more preferably provided in the form of gel beads. While beads are typically rounded or spheroidal in shape, this shape is normally a consequence of processing a matrix into a gel. In accordance with the present invention, the shape and/or size of the gel moiety is not critical so long as the gel moiety does not substantially interfere with the therapeutic action or adversely affect the desired properties of the water stable pharmaceutical compositions, liquid form oral pharmaceutical compositions, kits, and rehydration beverage compositions.

In certain embodiments, the compositions of the present invention are provided as part of an isotonic, supplemental nutrient, or rehydration beverage known in the art, for example, in U.S. Pat. No. 7,052,725 or U.S. Pat. No. 7,160,565, the disclosures of which are hereby incorporated herein by reference, in their entireties.

The liquid form oral pharmaceutical and/or beverage compositions of the present invention may also include additional ingredients such as purified water, sweeteners, edible acids, flavor compositions, preservative systems, caffeine, caramel, color agents, dyes, antifoam, and mineral or non-mineral nutritional supplements. The sweeteners used in the beverages can comprise any readily available natural and artificial sweetener known to be useful in edible compositions or rehydration beverages, or mixtures thereof, including complex carbohydrates known as useful in rehydration beverages, and in their usual concentrations. Since many who exercise do not want to ingest excess calories, the level of sugars used is kept low, preferably about 2 to 4% by weight of the beverage. However, there are often exercise-related needs for the ingestion of greater levels of carbohydrates, especially in the recovery from long duration exercise where carbohydrate (glucose) is needed to replace muscle glycogen. For dietetic beverages any artificial sweeteners stable in beverage use can be substituted fully or in part for the a typical sweetener. Artificial sweeteners useful in the liquid form oral pharmaceutical and/or beverage compositions of the present invention may also include peptide and non-peptide based artificial sweeteners and mixtures thereof. Peptide based sweeteners include, for example, aspartame, neotame, and alitame. Non-peptide based sweeteners include, for example, sodium saccharin, calcium saccharin, acesulfame potassium, sodium cyclamate, calcium cyclamate, neohesperidin, dihydrochalcone, and sucralose. In some applications, such as in caramel containing beverages, alitame may form a precipitate (somewhat less desirable) which may interfere with overall flavor impressions in the final product. In certain preferred embodiments, the artificial sweetener comprises aspartame. In other preferred embodiments, the sweetener comprises aspartame and acesulfame potassium. In still other preferred embodiments, the sweetener comprises sucralose.

The liquid form oral pharmaceutical and/or beverage compositions of the present invention may also include one or more flavor compositions, for example, fruit flavor compositions, botanical flavor compositions, or a mixture thereof. If the flavoring composition contains acid, it is also added to the stabilized solution prior to the addition of the artificial sweetener. Examples of acid-containing flavoring compositions include cola flavoring and citrus flavors.

The particular amount of the flavor component useful for imparting flavor characteristics to the beverages of the present invention will depend upon the flavor(s) selected, the flavor impression desired, and the form of the flavor component. Those skilled in the art are readily able to determine the amount of any particular flavor component(s) used to achieve the desired flavor impression.

The liquid form oral pharmaceutical and/or beverage compositions of the present invention may also include additional ingredients typically found in beverage formulations. Non-limiting examples of such additional ingredients include, but are not limited to, caffeine, caramel, coloring agents or dyes, antifoam, gums, emulsifiers, tea solids, juices, cloud component, and mineral and non-mineral nutritional supplements.

Examples of non-mineral nutritional supplement ingredients are known to those of ordinary skill in the art and include, without limitation, amino acids, oligopeptides, antioxidants and vitamins, including Vitamins A, D, E (tocopherol), C (ascorbic acid), B1 (thiamine), B2 (riboflavin), B6, B12, and K, niacin, folic acid, biotin, and combinations thereof. The optional non-mineral nutritional supplements are typically present in amounts generally accepted under good manufacturing practices and are preferably present in amounts between about 1% to about 100% RDV, where such RDV are established. When present, the non-mineral nutritional supplement ingredient(s) is preferably present in an amount of from about 5% to about 20% RDV, where established. In a particularly preferred embodiment, the beverage compositions of the invention contain Vitamin E, optionally with Vitamin C. Suitable amino acids include, but are not limited to, lysine, isoleucine, leucine, threonine, valine, tryptophan, phenylalanine, methionine and L-selenomethionine.

In addition to the minerals typically found in isotonic beverages such as sodium and potassium, other suitable minerals include, but are not limited to calcium, iron, zinc, vanadium, selenium, chromium, boron, potassium, manganese, copper and magnesium.

Other optional conventional liquid dosage form and/or beverage components would be readily apparent to one of ordinary skill in the art, once armed with the teachings of the present disclosure.

In other embodiments, the present invention provides processes for preparing the water stable pharmaceutical compositions of the invention described herein, comprising: contacting a therapeutic agent with an off-flavor masking agent and a precursor of a pharmaceutically acceptable matrix, preferably gel matrix, more preferably non-ion-specific gel matrix, in an aqueous medium, for a time and under conditions effective to provide a pharmaceutically acceptable matrix containing the therapeutic agent and the off-flavor masking agent. Preferably, the matrix containing the therapeutic agent and off-flavor masking agent is present in the form of beads. In other preferred embodiments, the matrix is isolated, separated, or removed from the aqueous medium by any of the methods known to one or ordinary skill in the art, such as for example, filtration or centrifugation, preferably filtration. The matrix, once isolated, separated, or removed from the aqueous medium, may optionally be rinsed or otherwise cleansed to reduce and/or minimize the presence of residual aqueous medium on the surface of the matrix.

Accordingly, in certain other embodiments, the present invention is directed to processes for preparing a liquid form oral pharmaceutical composition, comprising:
  contacting for a time and under conditions effective to provide said liquid form oral pharmaceutical composition:
  a water stable pharmaceutical composition; and
  a pharmaceutically acceptable aqueous liquid medium;
  wherein said water stable pharmaceutical composition comprises a therapeutic agent and an off-flavor masking agent in a pharmaceutically acceptable matrix.

In certain preferred embodiments of the processes for preparing a liquid form oral pharmaceutical composition, the water stable pharmaceutical composition is prepared by a process comprising contacting:
  a therapeutic agent, an off-flavor masking agent, and a precursor of a pharmaceutically acceptable gel matrix in an aqueous medium for a time and under conditions effective to provide the water stable pharmaceutical composition.

In certain preferred embodiments of the present invention, a complex of therapeutic agent and off-flavor masking agent is formed by contacting said therapeutic agent with said off-flavor masking agent in an aqueous medium for a time and under conditions effective to provide said complex. In other preferred embodiments, the complex of therapeutic agent and off-flavor masking agent in aqueous medium is contacted with a precursor of a pharmaceutically acceptable matrix, more preferably gel matrix, in an aqueous medium for a time and under conditions effective to form the pharmaceutically acceptable matrix, more preferably gel matrix, containing the therapeutic agent and the off-flavor masking agent in the aqueous medium. In certain more preferred embodiments, the complex of therapeutic agent and off-flavor masking agent is not isolated or purified prior to contact with the matrix precursor.

The water stable pharmaceutical compositions and/or liquid form oral pharmaceutical compositions of the present invention may be prepared in any number of ways known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

In processes for the preparation of water stable pharmaceutical compositions and/or liquid form oral pharmaceutical compositions of the present invention, the order of addition of the therapeutic agent, the off-flavor masking agent, and the pharmaceutically acceptable matrix precursor is not critical. Thus, the therapeutic agent, the off-flavor masking agent, and the pharmaceutically acceptable matrix precursor may be contacted in an aqueous environment in any order. For simplicity, they may be added consecutively or simultaneously into the vessel used for their preparation. In some preferred embodiments it is advantageous to first contact the therapeutic agent with the off-flavor masking agent in an aqueous environment, preferably forming at least a modicum of a therapeutic agent:off-flavor masking agent complex. It is unnecessary to isolate and/or purify the therapeutic agent/off-flavor masking agent mixture after they contact each other. The agents may associate, complex, or remain partially or completely unassociated. Once combined, the aqueous mixture of therapeutic agent/off-flavor masking agent may be contacted with a pharmaceutically acceptable matrix precursor for a time and under conditions effective to provide the water stable pharmaceutical composition in a pharmaceutically acceptable matrix. As would be apparent to the ordinarily skilled artisan, gellation of pharmaceutically acceptable gel matrices in the water stable pharmaceutically acceptable compositions of the present invention is clearly seen as occurring prior to the composition's administration to a patient, rather than in vivo, post administration of the composition.

As noted hereinabove, in certain preferred embodiments of water stable pharmaceutical compositions and/or liquid form oral pharmaceutical compositions, the off-flavor masking agent comprises a cyclic oligosaccharide. In some preferred embodiments, the cyclic oligosaccharide forms a complex or clathrate with the therapeutic agent. Typically these complexes may be represented by a 1:1 host-guest type of complex. In order to provide for a least a portion of the formed complex in the compositions of the present invention, some general guidance is helpful. While the molar ratio of cyclic oligosaccharide (or other host molecule) to therapeutic agent (or guest molecule) in the present compositions or methods of manufacture of the cyclic oligosaccharide:therapeutic agent complex is not critical, host:guest molar ratios of from about 20:1 to about 1:20 are typically employed. Preferably ratios from about 1:10 to about 10:1, more preferably from about 1:5 to about 5:1, with from about 2:1 to about 1:2 being even more preferred are employed in the compositions and/or methods of their preparation. While in theory a 1:1 molar ratio of cyclic oligosaccharide:therapeutic agent should be adequate to prepare the complex of substantially all of the therapeutic agent contained in the preparative solution, it is preferable in some embodiments to add at least a slight excess of the host molecule to increase the likelihood that substantially all of the guest therapeutic agent is complexed. As described herein, such complexation will assist in the improvement of stability, solubility and/or taste masking of the therapeutic agent. For purposes of general guidance, a molar excess of about 10%, 20, 30, 50, 75, or even 100% of the cyclic oligosaccharide to therapeutic agent on a molar basis is typically sufficient to complex substantially all of the therapeutic agent in the cyclic oligosaccharide. In certain alternative embodiments, it is preferable to employ from about a 1.8:1 to about a 1:1.8 molar ratio of cyclic oligosaccharide:therapeutic agent, more preferably from about 1.5:1 to about 1:1.5. still more preferably 1.25:1 to about 1:1.25, with from about 1.1:1 to about 1:1.1 even more preferred.

Alternatively, the therapeutic agent, preferably water-sensitive and/or bitter tasting therapeutic agent, and off-flavor masking agent, preferably cyclodextrin, may be dry blended together in any manner known in the art prior to their introduction into the aqueous environment in the processes for the preparation of the water stable pharmaceutical compositions of the present invention. In some preferred embodiments, this dry blending allows some degree of complexation or association, preferably complexation, to occur between the therapeutic agent and the off-flavor masking agent, preferably cyclodextrin, as may be understood by the ordinarily skilled artisan, once armed with the teachings of the present invention.

While not intending to be bound by any theory or theories of operation, it is contemplated that side effects resulting from administration of hydrolytic by-products of therapeutic agents may result from undesirable interaction of a water sensitive therapeutic agent with water. Thus, use of a water stable pharmaceutical composition, liquid form oral pharmaceutical composition, or rehydration beverage composition of the present invention may minimize the interaction of water with the therapeutic agent in an aqueous liquid form pharmaceutical composition, and thereby reduce the level of hydrolysis by-products that may lead to side effects as compared with prior art aqueous therapeutic agent delivery systems. By minimizing the water interaction with the therapeutic agent, shelf life may be improved and efficacy of the therapeutic agent may be maintained or less diminished than with some prior art methods to prevent or treat a disease, disorder, condition, or symptoms thereof in a patient in need thereof.

Any methods known to be useful for forming liquid form oral pharmaceutical or beverage compositions may be used to make the desired compositions.

The particular amount of the flavor component useful for imparting flavor characteristics to the beverages of the present invention will depend upon the flavor(s) selected, the flavor impression desired, and the form of the flavor component. Those skilled in the art are readily able to determine the amount of any particular flavor component(s) used to achieve the desired flavor impression.

The liquid form oral pharmaceutical and/or beverage compositions of the present invention may also include additional ingredients typically found in beverage formulations. Non-limiting examples of such additional ingredients include, but are not limited to, caffeine, caramel, coloring agents or dyes, antifoam, gums, emulsifiers, tea solids, juices, cloud component, and mineral and non-mineral nutritional supplements, including nutraceuticals and dietary supplements.

Exemplary nutraceuticals and dietary supplements are disclosed, for example, in Roberts et al., Nutraceuticals: The Complete Encyclopedia of Supplements, Herbs, Vitamins, and Healing Foods (American Nutraceutical Association, 2001), which is specifically incorporated by reference. A nutraceutical or dietary supplement, also known as phytochemicals or functional foods, is generally any one of a class of dietary supplements, vitamins, minerals, herbs, or healing foods that have medical or pharmaceutical effects on the body. Exemplary nutraceuticals or dietary supplements include, but are not limited to, lutein, folic acid, fatty acids (e.g., DHA and ARA), fruit and vegetable extracts, vitamin and mineral supplements, phosphatidylserine, lipoic acid, melatonin, glucosamine/chondroitin, Aloe Vera, Guggul, glutamine, amino acids (e.g., iso-leucine, leucine, lysine, methionine, phenylanine, threonine, tryptophan, and valine), green tea, lycopene, whole foods, food additives, herbs, phytonutrients, antioxidants, flavonoid constituents of fruits, evening primrose oil, flax seeds, fish and marine animal oils, and probiotics. Nutraceuticals and dietary supplements also include bio-engineered foods genetically engineered to have a desired property, also known as "pharmafoods." Examples of non-mineral nutritional supplement ingredients are known to those of ordinary skill in the art and include, without limitation, amino acids, oligopeptides, antioxidants and vitamins, including Vitamins A, D, E (tocopherol), C (ascorbic acid), B1 (thiamine), B2 (riboflavin), B6, B12, and K, niacin, folic acid, biotin, and combinations thereof. The optional non-mineral nutritional supplements are typically present in amounts generally accepted under good manufacturing practices and are preferably present in amounts between about 1% to about 100% RDV, where such RDV are established. When present, the non-mineral nutritional supplement ingredient(s) is preferably present in an amount of from about 5% to about 20% RDV, where established. In a particularly preferred embodiment, the beverage compositions of the invention contain Vitamin E, optionally with Vitamin C. Suitable amino acids include, but are not limited to, lysine, isoleucine, leucine, threonine, valine, tryptophan, phenylalanine, methionine and L-selenomethionine.

In addition to the minerals typically found in isotonic beverages such as sodium and potassium, other suitable minerals include, but are not limited to calcium, iron, zinc, vanadium, selenium, chromium, boron, potassium, manganese, copper and magnesium.

The water stable pharmaceutical compositions, liquid form oral pharmaceutical compositions, and/or beverage compositions of the present invention may be useful in prophylaxis and/or treatment of a variety of diseases, disorders, conditions, and or symptoms thereof including for example coughs, colds, and/or flu symptoms; gas, upset stomach, and diarrhea formulations, sinus allergies, and/or pain. Further, the compositions may find additional usage in one or more situations where administration of medications in the form of pills, tablets, or capsules cannot be practically administered (e.g. patient is incapable of swallowing a pill). Alternative means of administration are especially important for pediatric patients. Thus, the water stable pharmaceutical compositions, liquid form oral pharmaceutical compositions, and/or beverage compositions of the present invention may find use, for example, in beverages that provide a trouble-free way for parents to administer medications in a form with improved palatability to children, improve some aspects of general physical health (various health-related beverages, including active ingredients with probiotics, nutraceuticals, OPC (Oligomeric Procyanidins), herbal remedies, etc.), assist in the reduction of cholesterol levels in the body and/or deliver therapeutics such as nicotine that may reduce the urge to smoke and/or assist its smokers in combating their habituation of cigarette, cigar or pipe smoking.

Compounds as described herein may be administered to a mammalian host or "patient", such as a human host or patient, in a variety of forms adapted to the chosen oral route of administration.

The water stable pharmaceutical composition or liquid form oral pharmaceutical composition may be orally administered, for example, with an inert diluent. For oral therapeutic administration, the active compound may be incorporated with excipient and used in the form of elixirs, suspensions, syrups, and the like. The amount of active therapeutic agent(s) in such therapeutically useful compositions is preferably such that a suitable dosage, more preferably an amount equivalent to the typical recommended dosage over-the counter recommended dose, will be administered. For example, a typical over the counter unit dosage for ibuprofen is 200 mg every four to six hours. Therefore, a suitable dosage in certain embodiments of the invention would contain or provide 200 mg in a single dosage. Preferred compositions or preparations according to the present invention may be prepared so that an oral dosage unit form contains from about 0.1 to about 1000 mg of active therapeutic agent, and all combinations and subcombinations of ranges and specific amounts of active compound therein.

A syrup or elixir may contain the water stable pharmaceutical composition, as well as any of the other optional ingredients noted hereinabove, including, for example, sucrose as a sweetening agent, methyl and propylparabens as preservatives, a dye and flavoring, such as cherry or orange flavor. Of course, any material used in preparing any dosage unit form is preferably pharmaceutically pure and substantially non-toxic in the amounts employed. In addition, the active compound may be incorporated into sustained-release preparations and formulations.

The dosage of the therapeutic agent that comprises the water stable pharmaceutical compositions, liquid form oral pharmaceutical compositions, kits, and/or beverage compositions may vary depending upon various factors such as, for example, the pharmacodynamic characteristics of the particular agent and its mode and route of administration, the age, health and weight of the recipient, the nature and extent of the symptoms, the kind of concurrent treatment, the frequency of treatment, and the effect desired. Generally, small dosages may be used initially and, if necessary, increased by small increments until the desired effect under the circumstances is reached.

It will be further appreciated that the amount of the therapeutic agent, or an active salt or derivative thereof, required for use in treatment will vary not only with the particular agent or salt thereof selected but also with the route of administration the indication, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day.

The dose may also be provided by controlled release of the compound, by techniques well known to those in the art.

The disclosures of each of the foregoing documents are hereby incorporated herein by reference, in their entireties.

The present invention is further described in the following examples. Excepted where specifically noted, the examples are actual examples. These examples are for illustrative purposes only, and are not to be construed as limiting the appended claims.

EXPERIMENTAL SECTION

The beverage prototypes were prepared in a lab-scale setting, utilizing common laboratory glassware and equipment. All GRAS chemicals and raw materials were purchased from certified suppliers such as Sigma-Aldrich, Fisher Scientific, Acros Organics, CP Kelco, and Gold Coast Ingredients. Materials: all chemicals were reagent grade and used without further purification.

Heat Stable Testing Protocols

Retort Processing

To test the stability of the water stable pharmaceutical compositions in either liquid form oral pharmaceutical composition or rehydration beverage composition applications under retort conditions (121° C. at 15 PSI), 80 grams of the composition is added to an aluminum retort can (211×300 mm, Freund Container company, Chicago, Ill.) and filled with water at 80° C. The cans are sealed using a benchtop can sealer (Dixie Canning Company, Athens, Ga.), placed in a pilot scale retort (Dixie Canning Company, Athens, Ga.), and processed at 121° C. and 15 PSI for 55 minutes. Following the retort process, the can is opened. The excess water is removed and the beads are observed under a microscope. If the gel matrix of the beads is heat stable to retort conditions, the beads will appear intact. Further HPLC analysis of the beads and/or medium may provide further indication of heat stability if the therapeutic agent is water sensitive.

Hot Fill Processing

To test the stability of the gel matrix bead through hot fill conditions (104° C. at 15 PSI), the liquid form oral pharmaceutical composition or rehydration beverage composition is thermally processed (hot fill) using a MicroThermics pilot scale thermal processing unit. The mixture is processed with a flow of 500 mLs per minute configured for a 60 second retention time at 104° C. The product temperature at the fill spout should be about 82° C. and was captured in 250 ml media bottles. Once filled, the bottles are sealed with airtight screw cap lids and held upside down for 3 minutes to sterilize the lids. Following this, the bottles are cooled by submerging in a tank of ambient tap water. After completion of the hot fill process, the bottles are opened. The excess water is removed and the beads are observed under a microscope. If the gel matrix of the beads is heat stable to hot fill processing conditions, the beads will appear intact. Further HPLC analysis of the beads and/or medium may provide further indication of heat stability if the therapeutic agent is water sensitive.

Accelerated Stability Test Procedures

Each composition sample was placed in a 25 mL glass vial, which was in turn placed in a 55° C. oven. For prototypes which did not contain beads (such as 'liquid matrix' type compositions, or fluid-bed type compositions), the glass vial was completely filled with the liquid sample. For those composition containing gel beads, there was a 50/50 (w/v) of beads-to-liquid matrix (which together filled the glass container). Approximately 12.5 g of beads in 12.5 mL of liquid medium was needed to fill the vial.

HPLC Analysis Conditions for Accelerated Stability Test Procedures

ASA HPLC Method

Analysis of ASA degradation products was performed using an Agilent Technologies 1200 series HPLC with a PDA (photodiode array, detector wavelength 224 nm) detector, incorporating a Phenominex C18-2 column (25 cm×0.39 cm i.d., 5 μm particle size). Solvent system A) $H_2O$, Acetonitrile, Phosphoric Acid (95.45:4.5:0.05), and B) $H_2O$, Acetonitrile, Phosphoric Acid (49.95:50:0.05). Solvent B ramped from 10%-80% over 20 minutes. Stability was verified using peak area, which was used to determine the overall percentage of breakdown of ASA to salicylic acid. The injection volume for each sample tested was 5 micro-liters. The ratio of the area percent ASA peak (RT~17.7-18.2 minutes) and its hydrolysis product salicylic acid (peak at RT~19.3-19.4) were compared to determine the extent of hydrolysis over time.

Ibuprofen HPLC Method

A Zorbax Eclipse XDB-C8 4.6×150 mm 5 μm column was used with a Model 1260 Infinity HPLC system including diode array detector, refrigerated auto-injector, column oven, quaternary solvent pump and Chemstation operating software obtained from Agilent (Richmond Va.). Solvent was acetonitrile with 0.2% (v/v) triethylamine and adjusted to pH 3.2 with phosphoric acid at a flow rate of 1.5 ml/min. Injection volume was 5 μl. Stability was verified using peak area, which was used to determine the overall percentage of breakdown of drug (Ibuprofen). The area percent consistency of the given drug peak was used to determine the extent of stability over time.

Acetaminophen and Naproxen HPLC Method

Each of the analyses for acetaminophen and naproxen sodium was performed using an Agilent Technologies 1260 high performance liquid chromatograph equipped with a photodiode array (PDA) detector. Detection wavelength for acetaminophen was 248 nm and 330 nm for naproxen sodium. HPLC equipment included a Phenominex C18(2) column (25 cm×0.39 cm id, 5 μm particle size). Solvent system was a gradient from 90% A to 20% A over 20 minutes (solvent A: 95.45:4.5:0.5 water, acetonitrile, O-phosphoric acid, solvent B 49.95:50:0.05 water, acetonitrile, O-phosphoric acid). Injection volume was 5 μl. Stability was verified using peak area, which was used to determine the overall percentage of breakdown of drug (Acetaminophen or Naproxen). The area percent consistency of the given drug peak was used to determine the extent of stability over time.

Samples were removed from the vials (in the oven) at specific times and prepared for HPLC analysis. For the analysis of prototypes which contained only a liquid matrix (i.e., no beads), or when the liquid medium of a bead containing composition was analyzed, the following procedure was used to prepare the liquid sample for HPLC analysis.

A portion of liquid matrix (1 mL) was removed from the vial and added to a glass centrifuge tube. Methanol (MeOH, 1 mL) was then added to the centrifuge tube, shaken (vortexed), and left to stand for 1 hour. MeOH was used to assist in the removal and/or extraction of ASA from any of the encapsulation ingredients used (i.e., βCD, alginate, gellan, or any combination thereof). The sample was centrifuged for 15 minutes to spin down any particulates, and the top layer was removed for further HPLC analysis.

The preparation of bead samples for HPLC analysis was conducted using the following method. Bead material (1 gram) was removed from the vial and added to a glass centrifuge tube. Methanol (1 mL) was added to the centrifuge tube, and the beads were ground inside the tube (with the MeOH) using a small metal spatula until the beads were extremely fine particles (appeared completely blended to the human eye). The resultant was allowed to stand for 1 hour. The sample was centrifuged for 15 minutes to spin down particulates, and the top liquid layer was removed for further HPLC analysis.

EXAMPLES OF THE PRESENT INVENTION

Example 1

Step I. beta-Cyclodextrin and ASA Complex in Distilled Water

A 500 mL beaker was placed on a stir-plate. 87.65 mLs of Distilled water (DH2O) was poured into the beaker. beta-Cyclodextrin (βCD, 1.8 g) and acetylsalicylic acid (ASA, 143 mg) were added to the water to provide approximately a 2:1 molar ratio of beta-cyclodextrin to ASA. The mixture was stirred rapidly (using a stirring rod) for about 30 minutes.

Step II. Production of Gellan Microbeads Containing the βCD-ASA Complex 0.25 g Sodium citrate (trisodium citrate dihydrate) was dissolved in the aqueous mixture containing the βCD-ASA complex that was produced in step I above.

0.50 g of KELCOGEL F gellan gum powder, 0.01 g of KELTROL T xanthan gum powder, and 4 g sugar were dry blended together. The resulting blend was added to the citrate containing aqueous mixture and stirred rapidly until all solids were hydrated (i.e., no noticeable solids were present). 0.10 g of potassium sorbate and 7.50 g of sugar were then added to the mixture. The resultant mixture was stirred continuously until fully hydrated. A gel setting bath was prepared by dissolving 10 g of anhydrous citric acid in 90 mL DH2O. Similar procedures for preparing gels are found in the *Kelcogel Gellan Gum Book*, $5^{th}$ Ed., June 2007, incorporated herein by reference in its entirety. The fully hydrated mixture having the appearance of a viscous liquid was then loaded into a 50 mL syringe equipped with a 20 gauge needle to allow for the production of relatively small bead droplets. The viscous mixture was delivered dropwise from the syringe at an approximate rate of 1 mL/min into the setting bath. The liquid droplets immediately formed a solid gel bead upon contact with the setting bath. The newly formed gel beads were left in the setting bath for 1 hour, then isolated by filtration from the setting bath contents, and washed with DH2O.

Step III. Liquid Form Oral Pharmaceutical Composition

Into 100 mLs of DH2O, 12 g sugar, 0.2 g citric acid, 0.4 mL natural organic lemon flavor, 0.1 g natural masking agent, and 0.1 g sodium benzoate were added and allowed to completely dissolve via rapid stirring to form a liquid matrix portion (aqueous liquid medium) of a prototype liquid form oral pharmaceutical composition. The gellan gum gel beads (from part II above) were then added to the 100 mL liquid matrix. The gellan microbeads were suspended throughout the liquid matrix in the resulting composition.

Accelerated Storage Study for Example 1

Duplicate samples were stored for 40 days at 55° C. (equivalent to >400 days at 20° C. based on $Q_{10}=2$). HPLC analysis was performed on both the "bead portion" and "aqueous portion" of the prototype during the extent of the storage period. ASA was extracted from the bead portion using a 1:1 ratio (w:v) of methanol. After 40 days, the results of HPLC analysis (FIG. 1) for accelerated storage of ASA formulated with Gellan-βCD beads revealed that the new formulation provided remarkable ASA stability under these conditions (FIG. 2).

Sensory Evaluation of Example 1

Sensory evaluation of this composition showed that there was no ASA-derived off-flavor present. This approach provides for aqueous formulation of a highly stable ASA solution with no apparent off-flavor. Sensory testing also showed that there was no acetic acid off aroma.

Example 2

0.143 g ASA were complexed with 1.8 g βCD in 100 mLs of DIH2O. Added 2 g Alginate powder to the ASA/βCD mixture. The resultant was stirred until the alginate was fully hydrated. Beads were then made from this solution, in the same manner as described hereinabove for the Gellan beads, except the setting bath was Calcium Chloride solution (100 mM), which was made by adding 7.35 g Calcium Chloride to 500 mL distilled water. The beads were then added to the liquid matrix, prepared in analogous fashion to the Gellan beads in Example 1. The storage stability study was carried out in the same manner as the Gellan (bead) prototype.

Accelerated Storage Study of Example 2

FIG. 3 depicts an HPLC chromatogram of beads prepared by the procedure provided in Example 2. The beads were stable over the duration of the accelerated storage study. The graph in FIG. 4 compares the stability of ASA formulated in alginate/βCD bead composition to stability of ASA in water.

Sensory Evaluation of Example 2

Due to the inherent off-flavor originating from ASA and other analgesic drugs, the Example 2 composition was evaluated for its sensory characteristics. It was found that the formulation had an unidentified off-flavor.

Reduced Size Gellan Beads

Beads of smaller particle size that more closely approximate the range estimated for use in a commercial formulation were prepared to measure and compare the release kinetics of smaller beads (micron sized) with earlier prepared 2-3 mm sized beads. The gellan formulation utilized in this experiment was made by a procedure analogous to the process described in Example 1.

To prepare the smaller beads, an air aspirator was used to spray the gellan onto the citric acid solution. This setup was devised to approximate commercial preparation employing manufacturing equipment such as that provided by NISCO, with the exception that NISCO equipment uses a pump to deliver the solution to be sprayed while our system used was venturi-effect driven.

The beads (pre-bead composition doped with red food color before gellation) were examined by microscopy to determine using a Nikon Eclipse E400 microscope with coverslip and examined at 400×. Due to the non-spherical nature and varying size of the particles, an average diameter could not be obtained.

In Vitro Digestion Study—Simulated Gastric Digestion

A test simulating conditions in the stomach was conducted to assess rate of release of a therapeutic agent in an aqueous delivery system of the present invention. These conditions were simulated in the following manner. Into a solution containing pepsin (1 mg/ml pepsin) was added 4 N HCl dropwise to a final pH of 2.0. The pepsin solution (40 ml) was added to 50 ml screw cap tubes containing either 5 g of α-CD-ASA-Gellan or β-CD-ASA-Gellan beads prepared by a process analogous to that described in Example 1. After stifling the beads to disperse them in the pepsin solution, the pH of the mixture of sample and pepsin solution was adjusted to 2.0 with 4 N HCl to mimic the gastric phase. The mixture was digested in a shaker water bath at 120 rpm at 37° C. for 1 hour. At 5, 10, 40 and 60 minutes, samples of the aqueous component were taken, the aqueous sample centrifuged at 2000×g for 10 minutes at 4° C., and supernatant analyzed for free ASA by HPLC using the method hereinabove described.

FIG. 5 shows the release kinetics of ASA from the Gellan-βCD in vitro digestion model system (digestion at 37° C. for 60 minutes). The results show that increasing amounts of ASA were released from the Gellan-βCD bead formulation over a 20 minute period.

Example 3

Ibuprofen

Step I. Hydroxypropyl beta-Cyclodextrin (HPβCD) and Ibuprofen Complex in Distilled Water A 500 mL beaker was placed on a stir-plate. 87.65 mL of distilled water (DH2O) was poured into the beaker. Hydroxypropyl beta-cyclodextrin (HPβCD, 2.18 g) and ibuprofen (163.7 mg) were added to the water to provide approximately a 2:1 molar ratio of Hydroxypropyl beta-cyclodextrin to ibuprofen. The mixture was stirred rapidly (using a stirring rod) for about 30 minutes.

Step II. Production of Gellan Microbeads Containing the HPβCD-Ibuprofen Complex 0.25 g Sodium citrate (trisodium citrate dihydrate) was dissolved in the aqueous mixture containing the HPβCD-Ibuprofen complex that was produced in step I above.

0.50 g of KELCOGEL F gellan gum powder, 0.01 g of KELTROL T xanthan gum powder, and 4 g sugar were dry blended together. The resulting blend was added to the citrate containing aqueous mixture and stirred rapidly until all solids were hydrated (i.e., no noticeable solids were present). 0.10 g of potassium sorbate and 7.50 g of sugar were then added to the mixture. The resultant mixture was stirred continuously until fully hydrated. A gel setting bath was prepared by dissolving 10 g of anhydrous citric acid in 90 mLs DH2O. Similar procedures for preparing gels are found in the Kelcogel Gellan Gum Book 5th Ed., June 2007. The fully hydrated mixture having the appearance of a viscous liquid was then loaded into a 50 mL syringe equipped with a 20 gauge needle to allow for the production of relatively small bead droplets. The viscous mixture was delivered drop-wise from the syringe at an approximate rate of 1 mL/min into the setting bath. The liquid droplets immediately formed a solid gel bead upon contact with the setting bath. The newly formed gel beads were left in the setting bath for 1 hour, then isolated by filtration from the setting bath contents, and washed with DH2O.

Step III. Liquid From Oral Pharmaceutical Composition

Into 100 mL of DH2O, 12 g sugar, 0.2 g citric acid, 0.4 mL natural organic lemon flavor, 0.1 g natural masking agent, and 0.1 g sodium benzoate were added and allowed to completely dissolve via rapid stirring to form a liquid matrix portion (aqueous liquid medium) of a prototype liquid form oral pharmaceutical composition. The gellan gum gel beads (from part II above) were then added to the 100 mL liquid matrix. The gellan microbeads were suspended throughout the liquid matrix in the resulting composition.

Accelerated Storage Study for Example 3

Duplicate samples were stored for 21 days at 55° C. (equivalent to 36 weeks at 20° C. if Q10=2). HPLC analysis was performed on the "bead portion" of the prototype during the extent of the storage period. Ibuprofen was extracted from the bead portion using a 1:1 ratio (w:v) of methanol. After 21 days, the results of HPLC analysis (FIG. 6a) for accelerated storage of ibuprofen formulated with Gellan-HPβCD beads revealed that the new formulation provided remarkable ibuprofen stability under these conditions. No breakdown was observed for ibuprofen during the storage period. Stability was verified using peak area, which was used to determine the overall percentage of breakdown of drug (ibuprofen). The area percent consistency of the given drug peak was used to determine the extent of stability over time. FIG. 6b shows consistent stability of ibuprofen over the extent of the storage period.

Sensory Evaluation of Example 3 (Ibuprofen)

Sensory evaluation of this composition showed that there was no ibuprofen-derived off-flavor present. This approach provides for aqueous formulation of a highly stable ibuprofen solution with no apparent off-flavor.

Example 4

Acetaminophen

Step I. Hydroxypropyl beta-Cyclodextrin (HPβCD) and Acetaminophen Complex in Distilled Water A 500 mL beaker was placed on a stir-plate. 87.65 mLs of Distilled water (DH2O) was poured into the beaker. Hydroxypropyl-beta-cyclodextrin (HPβCD, 2.18 g) and acetaminophen (120 mg) were added to the water to provide approximately a 2:1 molar ratio of Hydroxypropyl beta-cyclodextrin to acetaminophen. The mixture was stirred rapidly (using a stirring rod) for about 30 minutes.

Step II. Production of Gellan Microbeads Containing the HPβCD-Acetaminophen Complex 0.25 g Sodium citrate (trisodium citrate dihydrate) was dissolved in the aqueous mixture containing the HPβCD-acetaminophen complex that was produced in step I above.

0.50 g of KELCOGEL F gellan gum powder, 0.01 g of KELTROL T xanthan gum powder, and 4 g sugar were dry blended together. The resulting blend was added to the citrate containing aqueous mixture and stirred rapidly until all solids were hydrated (i.e., no noticeable solids were present). 0.10 g of potassium sorbate and 7.50 g of sugar were then added to the mixture. The resultant mixture was stirred continuously until fully hydrated. A gel setting bath was prepared by dissolving 10 g of anhydrous citric acid in 90 mLs DH2O. Similar procedures for preparing gels are found in the Kelcogel Gellan Gum Book, 5th Ed., June 2007. The fully hydrated mixture having the appearance of a viscous liquid was then loaded into a 50 mL syringe equipped with a 20 gauge needle to allow for the production of relatively small bead droplets. The viscous mixture was delivered drop-wise from the syringe at an approximate rate of 1 mL/min into the setting bath. The liquid droplets immediately formed a solid gel bead upon contact with the setting bath. The newly formed gel beads were left in the setting bath for 1 hour, then isolated by filtration from the setting bath contents, and washed with DH2O.

Step III. Liquid From Oral Pharmaceutical Composition

Into 100 mLs of DH2O, 12 g sugar, 0.2 g citric acid, 0.4 mL natural organic lemon flavor, 0.1 g natural masking agent, and 0.1 g sodium benzoate were added and allowed to completely dissolve via rapid stirring to form a liquid matrix portion (aqueous liquid medium) of a prototype liquid form oral pharmaceutical composition. The gellan gum gel beads (from part II above) were then added to the 100 mL liquid matrix. The gellan microbeads were suspended throughout the liquid matrix in the resulting composition.

Accelerated Storage Study for Example 4 (Acetaminophen)

Duplicate samples were stored for 21 days at 55° C. (equivalent to 36 weeks at 20° C. if Q10=2). HPLC analysis was performed on the "bead portion" of the prototype during the extent of the storage period. Acetaminophen was extracted from the bead portion using a 1:1 ratio (w:v) of methanol. After 21 days, the results of HPLC analysis for accelerated storage of acetaminophen formulated with Gellan-HPβCD beads revealed that the new formulation provided remarkable acetaminophen stability under these conditions (FIG. 7). No breakdown was observed for acetaminophen during the storage period. Stability was verified using peak area, which was used to determine the overall percentage of breakdown of drug (acetaminophen). The area percent consistency of the given drug peak was used to determine the extent of stability over time.

Sensory Evaluation of Example 4 (Acetaminophen)

Sensory evaluation of this composition showed that there was no acetaminophen-derived off-flavor present. This approach provides for aqueous formulation of a highly stable acetaminophen solution with no apparent off-flavor.

Example 5

Naproxen Sodium

Step I. Hydroxypropyl beta-Cyclodextrin (HPβCD) and Naproxen Sodium Complex in Distilled Water A 500 mL beaker was placed on a stir-plate. 87.65 mLs of Distilled water (DH2O) was poured into the beaker. Hydroxypropyl-beta-cyclodextrin (HPβCD, 2.18 g) and naproxen sodium (200.2 mg) were added to the water to provide approximately a 2:1 molar ratio of Hydroxypropyl-beta-cyclodextrin to naproxen sodium. The mixture was stirred rapidly (using a stirring rod) for about 30 minutes.

Step II. Production of Gellan Microbeads Containing the HPβCD-Naproxen Sodium Complex 0.25 g Sodium citrate (trisodium citrate dihydrate) was dissolved in the aqueous mixture containing the HPβCD-naproxen sodium complex that was produced in step I above.

0.50 g of KELCOGEL F gellan gum powder, 0.01 g of KELTROL T xanthan gum powder, and 4 g sugar were dry blended together. The resulting blend was added to the citrate containing aqueous mixture and stirred rapidly until all solids were hydrated (i.e., no noticeable solids were present). 0.10 g of potassium sorbate and 7.50 g of sugar were then added to the mixture. The resultant mixture was stirred continuously until fully hydrated. A gel setting bath was prepared by dissolving 10 g of anhydrous citric acid in 90 mLs DH2O. Similar procedures for preparing gels are found in the Kelcogel Gellan Gum Book, 5th Ed., June 2007. The fully hydrated mixture having the appearance of a viscous liquid was then loaded into a 50 mL syringe equipped with a 20 gauge needle to allow for the production of relatively small bead droplets. The viscous mixture was delivered drop-wise from the syringe at an approximate rate of 1 mL/min into the setting bath. The liquid droplets immediately formed a solid gel bead upon contact with the setting bath. The newly formed gel beads were left in the setting bath for 1 hour, then isolated by filtration from the setting bath contents, and washed with DH2O.

Step III. Liquid From Oral Pharmaceutical Composition

Into 100 mLs of DH2O, 12 g sugar, 0.2 g citric acid, 0.4 mL natural organic lemon flavor, 0.1 g natural masking agent, and 0.1 g sodium benzoate were added and allowed to completely dissolve via rapid stirring to form a liquid matrix portion (aqueous liquid medium) of a prototype liquid form oral pharmaceutical composition. The gellan gum gel beads (from part II above) were then added to the 100 mL liquid matrix. The gellan microbeads were suspended throughout the liquid matrix in the resulting composition.

Accelerated Storage Study for Example 5 (Naproxen Sodium)

Duplicate samples were stored for 21 days at 55° C. (equivalent to 36 weeks at 20° C. if Q10=2). HPLC analysis was performed on the "bead portion" of the prototype during the extent of the storage period. Naproxen sodium was extracted from the bead portion using a 1:1 ratio (w:v) of methanol. After 21 days, the results of HPLC analysis for accelerated storage of naproxen sodium formulated with Gellan-HPβCD beads revealed that the new formulation provided remarkable naproxen sodium stability under these conditions (FIG. 8). No breakdown was observed for acetaminophen during the storage period. Stability was verified using peak area, which was used to determine the overall percentage of breakdown of drug (naproxen sodium). The area percent consistency of the given drug peak was used to determine the extent of stability over time.

Sensory Evaluation of Example 5 (Naproxen Sodium)

Sensory evaluation of this composition showed that there was no naproxen sodium-derived off-flavor present. This approach provides for aqueous formulation of a highly stable naproxen sodium solution with no apparent off-flavor.

COMPARATIVE EXAMPLES

Figure 9:
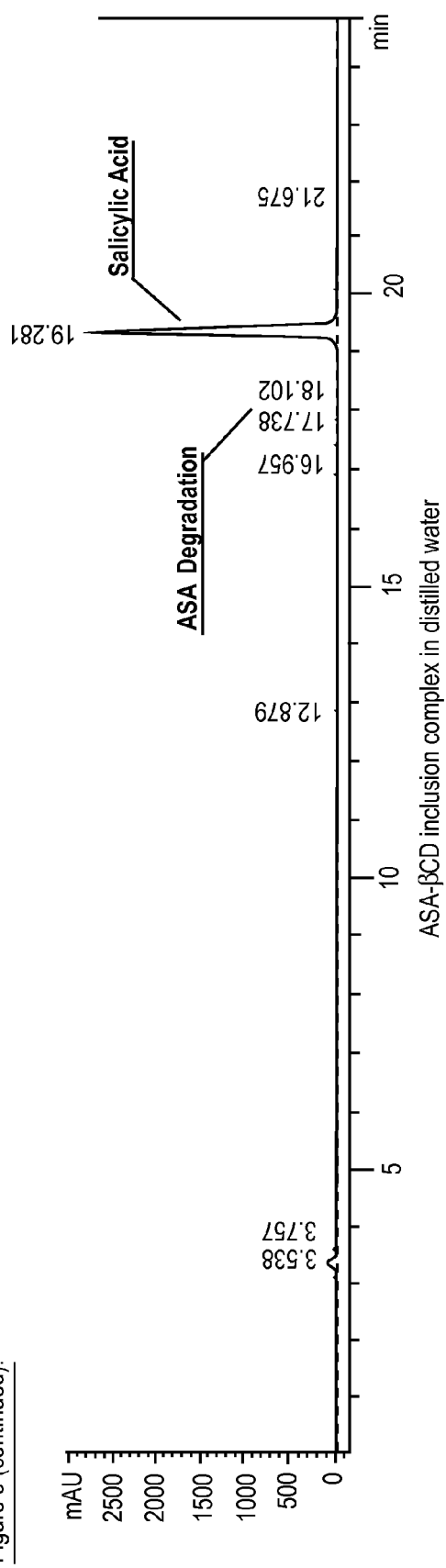
FIG. 9 depicts three HPLC chromatograms showing ASA instability in distilled water after 3 weeks at 45° C. The initial chromatogram is an analysis of an ASA standard the middle chromatogram gives an analytical indication of the stability of ASA in distilled water, the latter chromatogram is an analysis of stability of an ASA-βCD inclusion complex in distilled water.

Accelerated storage studies were conducted to examine the stability of ASA in distilled water, ASA in acidified (1% citric acid) distilled water, and of a molecular inclusion complex of ASA-βCD (in distilled water). Duplicate samples of each treatment were made containing 143 mg of ASA in 8 oz of distilled water. For the treatment containing the ASA-βCD complex, a 2:1 ratio of βCD to ASA was used as described in part I of the prototype formulation procedure outlined above. The treatments were stored at 45° C. for 3 weeks to determine the rate of hydrolysis of ASA to its breakdown product salicylic acid. Analysis of degradation products was performed using an Agilent Technologies 1200 series HPLC with a PDA (photodiode array) detector, incorporating a Phenominex C18-2 column (25 cm×0.39 cm i.d., 5 μm particle size). Solvent system A) $H_2O$, Acetonitrile, Phosphoric Acid (95.45:4.5:0.05), and B) $H_2O$, Acetonitrile, Phosphoric Acid (49.95:50:0.05). Solvent B ramped from 10%-80% over 20 minutes. Stability was verified using peak area, which was used to determine the overall percentage of breakdown of ASA to salicylic acid. FIG. 9 shows the nearly quantitative breakdown of ASA to salicylic acid in distilled water and for ASA molecularly encapsulated with β-cyclodextrin in distilled water during the accelerated storage study. Similar results were obtained for water acidified with citric acid. The sensory profile of the βCD-ASA solution was evaluated. It was found that the complex had no unpleasant taste.

Comparative Example

ASA-Gellan Formulation, w/o Cyclodextrin

Step I. ASA in Distilled Water

A 500 mL beaker is placed on a stir-plate. 87.65 mL of Distilled water (DH2O) is poured into the beaker. Acetylsalicylic acid (ASA, 143 mg) is added to the water. The mixture is stirred rapidly (using a stirring rod) until the ASA is fully dissolved.

Step II. Production of Gellan Microbeads Containing ASA 0.25 g Sodium citrate (trisodium citrate dihydrate) is dissolved in the aqueous mixture containing the ASA that is produced in step I above.

0.50 g of KELCOGEL F gellan gum powder, 0.01 g of KELTROL T xanthan gum powder, and 4 g sugar is dry blended together. The resulting blend is added to the citrate containing aqueous mixture and stirred rapidly until all solids are hydrated (i.e., no noticeable solids present). 0.10 g of potassium sorbate and 7.50 g of sugar is then added to the mixture. The resultant mixture is stirred continuously until fully hydrated. A gel setting bath is prepared by dissolving 10 g of anhydrous citric acid in 90 mLs DH2O. Similar procedures for preparing gels are found in the Kelcogel Gellan Gum Book, 5th Ed., June 2007. The fully hydrated mixture having the appearance of a viscous liquid is then loaded into a 50 mL syringe equipped with a 20 gauge needle to allow for the production of relatively small bead droplets. The viscous mixture is delivered dropwise from the syringe at an approximate rate of 1 mL/min into the setting bath. The liquid droplets immediately form a solid gel bead upon contact with the setting bath. The newly formed gel beads are left in the setting bath for 1 hour, then isolated by filtration from the setting bath contents, and washed with DH2O. Analysis of the beads indicates that the ASA has dydrolyzed to salicylic acid.

Step III. Liquid Form Oral Pharmaceutical Composition

Into 100 mL of DH2O, 12 g sugar, 0.2 g citric acid, 0.4 mL natural organic lemon flavor, 0.1 g natural masking agent, and 0.1 g sodium benzoate are added and allowed to completely dissolve via rapid stirring to form a liquid matrix portion (aqueous liquid medium) of a prototype liquid form oral pharmaceutical composition. The gellan gum gel beads (from part II above) are then added to the 100 mL liquid matrix. The gellan microbeads are suspended throughout the liquid matrix in the resulting composition. The composition tastes bitter.

Embodiment 1

A water stable pharmaceutical composition comprising:
a therapeutic agent; and
an off-flavor masking agent;
in a water stable pharmaceutically acceptable gel matrix;
wherein the water stable pharmaceutically acceptable gel matrix comprises a non-ion-specific gel.

Embodiment 2

The water stable pharmaceutical composition of Embodiment 1, wherein the therapeutic agent is water sensitive.

Embodiment 3

The water stable pharmaceutical composition of Embodiment 1 or 2, wherein the non-ion-specific gel comprises a polysaccharide.

Embodiment 4

The water stable pharmaceutical composition of Embodiment 3, wherein the polysaccharide comprises gellan.

Embodiment 5

The water stable pharmaceutical composition of any one of Embodiments 1, 2, 3, and 4, wherein the off-flavor masking agent comprises a cyclic oligosaccharide.

Embodiment 6

The water stable pharmaceutical composition of Embodiment 5, wherein the cyclic oligosaccharide contains from about 5 to about 10 monosaccharide units.

Embodiment 7

The water stable pharmaceutical composition of Embodiment 6, wherein the cyclic oligosaccharide comprises a cyclodextrin.

Embodiment 8

The water stable pharmaceutical composition of Embodiment 7, wherein the cyclodextrin comprises alpha-, beta-, or gamma-cyclodextrin, or a derivative or mixture thereof.

Embodiment 9

The water stable pharmaceutical composition of Embodiment 7 or 8, wherein the cyclodextrin comprises beta-cyclodextrin, or a derivative thereof.

Embodiment 10

The water stable pharmaceutical composition of Embodiment 7 or 8, wherein the cyclodextrin comprises alpha-cyclodextrin, or a derivative thereof.

Embodiment 11

The water stable pharmaceutical composition of any of Embodiments 1 to 10, wherein the therapeutic agent is selected from the group consisting of aspirin, naproxen sodium, acetaminophen, and ibuprofen.

Embodiment 12

The water stable pharmaceutical composition of any of Embodiments 1 to 10, wherein the therapeutic agent is ibandronate sodium.

Embodiment 13

The water stable pharmaceutical composition of any one of Embodiments 7 to 12, wherein at least a portion of the cyclodextrin and at least a portion of the therapeutic agent are present in the pharmaceutical composition as a therapeutic agent:cyclodextrin complex.

Embodiment 14

The water stable pharmaceutical composition of any one of Embodiments 7 to 13, wherein a substantial portion of the therapeutic agent is complexed with the cyclodextrin.

Embodiment 15

The water stable pharmaceutical composition any one of Embodiments 7 to 14, wherein substantially all of the therapeutic agent is complexed with the cyclodextrin.

Embodiment 16

The water stable pharmaceutical composition of any one of Embodiments 1 to 9 and 11, and 13 to 15, wherein:
  the therapeutic agent is selected from the group consisting of aspirin, naproxen sodium, acetaminophen, and ibuprofen;
  the off-flavor masking agent is beta-cyclodextrin; and
  the water stable pharmaceutically acceptable gel matrix comprises gellan.

Embodiment 17: The water stable pharmaceutical composition of any one of Embodiments 1 to 8, 10, 11, and 13 to 15, wherein:
  the therapeutic agent is selected from the group consisting of aspirin, naproxen sodium, acetaminophen, and ibuprofen;
  the off-flavor masking agent is alpha-cyclodextrin; and
  the water stable pharmaceutically acceptable gel matrix comprises gellan.

Embodiment 18: The water stable pharmaceutical composition of any one of Embodiments 1 to 9, 11, and 13 to 15, wherein:
  the therapeutic agent is selected from the group consisting of aspirin, naproxen sodium, acetaminophen, and ibuprofen;
  the off-flavor masking agent is hydroxypropyl beta-cyclodextrin; and
  the water stable pharmaceutically acceptable gel matrix comprises gellan.

Embodiment 19

The water stable pharmaceutical composition any one of Embodiment 1 to 11 and 13 to 18, wherein the therapeutic agent is aspirin.

Embodiment 20

The water stable pharmaceutical composition of any one of Embodiments 1 to 11 and 13 to 18, wherein the therapeutic agent is naproxen sodium.

Embodiment 21

The water stable pharmaceutical composition of any one of Embodiments 1 to 11 and 13 to 18, wherein the therapeutic agent is acetaminophen.

Embodiment 22

The water stable pharmaceutical composition of any one of Embodiments 1 to 11 and 13 to 18, wherein the therapeutic agent is ibuprofen.

Embodiment 23

The water stable pharmaceutical composition of any one of Embodiments 1 to 9, and 12 to 15, wherein:
  the therapeutic agent is ibandronate sodium;
  the off-flavor masking agent is beta-cyclodextrin; and
  the water stable pharmaceutically acceptable gel matrix comprises gellan.

Embodiment 24

The water stable pharmaceutical composition of any one of Embodiments 1 to 8, 10, and 12 to 15, wherein:
  the therapeutic agent is ibandronate sodium;
  the off-flavor masking agent is alpha-cyclodextrin; and
  the water stable pharmaceutically acceptable gel matrix comprises gellan.

Embodiment 25

The water stable pharmaceutical composition of any one of Embodiments 1 to 9 and 12 to 15, wherein:
  the therapeutic agent is ibandronate sodium;
  the off-flavor masking agent is hydroxypropyl beta-cyclodextrin; and
  the water stable pharmaceutically acceptable gel matrix comprises gellan.

Embodiment 26

The water stable pharmaceutical composition of any one of Embodiments 1 to 25, wherein the gel matrix is provided in the form of beads. Embodiment 27

The water stable pharmaceutical composition of any one of Embodiments 1 to 26 in a liquid oral dosage form.

Embodiment 28

A liquid form oral pharmaceutical composition; comprising:
  the water stable pharmaceutical composition of any one of Embodiments 1 to 27; and
  a pharmaceutically acceptable aqueous liquid medium.

Embodiment 29: A rehydration beverage composition, comprising:
  the water stable pharmaceutical composition of any one of Embodiments 1 to 27;
  optionally mineral or non-mineral nutritional supplements; and a pharmaceutically acceptable aqueous liquid medium;
wherein the aqueous medium comprises an isotonic solution.

Embodiment 30

A kit, comprising:
a. a liquid form oral pharmaceutical composition of Embodiment 28 in one or more containers; and
b. instructions for administering the liquid form oral pharmaceutical composition.

Embodiment 31

A process for preparing a water stable pharmaceutical composition comprising:
a therapeutic agent; and
an off-flavor masking agent;
in a water stable pharmaceutically acceptable gel matrix;
wherein the water stable pharmaceutically acceptable gel matrix comprises a non-ion-specific gel;
said process comprising contacting:
the therapeutic agent;
the off-flavor masking agent; and
a pharmaceutically acceptable gel matrix precursor;
in an aqueous medium with for a time and under conditions effective to provide the water stable pharmaceutical composition of any one of Embodiments 1 to 27.

Embodiment 32

The process for preparing a water stable pharmaceutical composition of Embodiment 31, wherein the cyclodextrin is first contacted with the therapeutic agent in an aqueous solution to form a cyclodextrin:therapeutic agent complex.

Embodiment 33

The process for preparing a water stable pharmaceutical composition of Embodiment 31 or 32, wherein the cyclodextrin:therapeutic agent complex in aqueous solution is contacted with the pharmaceutically acceptable gel matrix precursor, wherein said precursor comprises gellan, to form the pharmaceutically acceptable water stable gel matrix of the complex in an aqueous medium.

Embodiment 34

The kit of Embodiment 30, wherein the liquid form oral pharmaceutical composition in the kit container provides an individual dosage unit of therapeutic agent.

Embodiment 35

The water stable pharmaceutical composition of any one of Embodiments 1 to 27, wherein the therapeutic agent retains substantially all of its pre-retort or pre-hot-fill therapeutic efficacy after the water stable pharmaceutical composition is exposed to retort processing at 121° C. and 15 PSI for 60 minutes, or hot fill pasteurization at 104° C.

Embodiment 36: The water stable pharmaceutical composition of any one of Embodiments 1 to 27, wherein the therapeutic agent retains substantially all of its pre-UHT processing therapeutic efficacy or pre-HTST processing therapeutic efficacy after the water stable pharmaceutical composition is exposed to UHT processing conditions of about 1 to about 2 seconds at a temperature exceeding 135° C., or HTST pasteurization conditions of about 72° C. for at least 15 seconds.

When any variable occurs more than one time in any constituent or in any formula, its definition in each occurrence is independent of its definition at every other occurrence. Combinations of substituents and/or variables are permissible only if such combinations result in stable compositions.

It is believed the chemical formulas, abbreviations, and names used herein correctly and accurately reflect the underlying compounds reagents and/or moieties. However, the nature and value of the present invention does not depend upon the theoretical correctness of these formulae, in whole or in part. Thus it is understood that the formulas used herein, as well as the chemical names and/or abbreviations attributed to the correspondingly indicated compounds, are not intended to limit the invention in any way, including restricting it to any specific form or to any specific isomer.

When ranges are used herein for physical properties, such as molecular weight, or chemical properties, such as chemical formulae, all combinations and subcombinations of ranges and specific embodiments therein are intended to be included.

The disclosures of each patent, patent application and publication cited or described in this document are hereby incorporated herein by reference, in their entirety.

The invention illustratively disclosed herein suitably may be practiced in the absence of any element which is not specifically disclosed herein. The invention illustratively disclosed herein suitably may also be practiced in the absence of any element which is not specifically disclosed herein and that does not materially affect the basic and novel characteristics of the claimed invention.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A water stable pharmaceutical gel composition comprising:
a therapeutic agent selected from the group consisting of aspirin, naproxen sodium, acetaminophen, and ibuprofen; and
an off-flavor masking agent comprising a cyclodextrin;
in a water stable pharmaceutically acceptable gel matrix;
wherein:
the water stable pharmaceutically acceptable gel matrix comprises as non-ion-specific gel comprising gellan; and
wherein the water stable pharmaceutical gel composition is suitable for oral delivery of the therapeutic agent.

2. A water stable pharmaceutical composition of claim 1, wherein the therapeutic agent is an anti-inflammatory agent.

3. A water stable pharmaceutical composition of claim 1, wherein the therapeutic neat is water-sensitive.

4. A water stable pharmaceutical composition of claim 1, wherein the cyclodextrin comprises alpha-, beta-, or gamma-cyclodextrin., or a derivative or mixture thereof.

5. A water stable pharmaceutical composition of claim 4, wherein the cyclodextrin comprises beta-cyclodextrin, or a derivative thereof.

6. A water stable pharmaceutical composition of claim 4, wherein the cyclodextrin comprises alpha-cyclodextrin, or a derivative thereof.

7. A water stable pharmaceutical composition of claim 4, wherein at least a portion of the cyclodextrin and at least a portion of the therapeutic agent are present in the pharmaceutical composition as a therapeutic agent:cyclodextrin complex.

8. A water stable pharmaceutical composition of claim 2, wherein:
the off-flavor masking agent is beta-cyclodextrin or hydroxypropyl beta-cyclodextrin.

9. A water stable pharmaceutical composition of claim 8, wherein the therapeutic agent is aspirin.

10. A water stable pharmaceutical composition of claim 8, wherein the therapeutic agent is naproxen sodium.

11. A water stable pharmaceutical composition of claim 8, wherein the therapeutic agent is acetaminophen.

12. A water stable pharmaceutical composition of claim 8, wherein the therapeutic agent is ibuprofen.

13. A water stable pharmaceutical composition of claim 8, wherein the gellan matrix is provided in the form of beads.

14. A water stable pharmaceutical composition of claim 2, wherein:
the off-flavor masking agent is alpha-cyclodextrin.

15. A water stable pharmaceutical composition of claim 14, wherein the therapeutic agent is aspirin.

16. A water stable pharmaceutical composition of claim 14, wherein the therapeutic agent is naproxen sodium.

17. A water stable pharmaceutical composition of claim 14, wherein the therapeutic agent is acetaminophen.

18. A water stable pharmaceutical composition of claim 14, wherein the therapeutic agent is ibuprofen.

19. A liquid form oral pharmaceutical composition; comprising:
a water stable pharmaceutical composition according to claim 1; and
a pharmaceutically acceptable aqueous liquid medium.

20. A liquid form oral pharmaceutical composition of claim 19, wherein at least a portion of the cyclodextrin and at least a portion of the therapeutic agent are present as a therapeutic agent:cyclodextrin complex in the pharmaceutical composition.

21. A process for preparing a water stable pharmaceutical composition, said process comprising the steps of contacting:
a therapeutic agent selected from the group consisting of aspirin, naproxen sodium, acetaminophen, and ibuprofen;
an off-flavor masking agent comprising a cyclodextrin;
a pharmaceutically acceptable gel matrix precursor comprising a non-ion-specific polysaccharide gelling agent comprising gellan; and
water:
for a time and under conditions effective to provide a hydrated mixture; and
gelling said mixture in an aqueous citric acid medium with for a time and under conditions effective to provide said water stable pharmaceutical composition.

22. A process for preparing a water stable pharmaceutical composition of claim 21, wherein the cyclodextrin is first contacted with the therapeutic agent in an aqueous solution to form a cyclodextrin: therapeutic agent complex.

23. A kit, comprising:
a liquid form oral pharmaceutical composition of claim 19 in one or more containers; and
b. instructions for administering the liquid form oral pharmaceutical composition.

24. A kit of claim 23, wherein the liquid form oral pharmaceutical composition in the kit container is provided as an individual dosage unit of therapeutic agent.

25. A rehydration beverage composition, comprising:
a water stable pharmaceutical composition according; to claim 1:
a pharmaceutically acceptable aqueous liquid medium; and
optionally at least one mineral or non-mineral nutritional supplement;
wherein:
the aqueous medium comprises an isotonic solution.

26. A water stable pharmaceutical gel composition consisting essentially of:
a therapeutic agent selected from the group consisting of aspirin, naproxen sodium, acetaminophen, and ibuprofen; and
an off-flavor masking agent comprising a cyclodextrin,
in a water stable pharmaceutically acceptable gel matrix;
wherein the water stable pharmaceutically acceptable gel matrix comprises a non-ion-specific gel comprising gellan.

27. A water stable pharmaceutical gel composition according, to claim 1, wherein the water stable pharmaceutical gel composition is further:
substantially stable in the presence of an aqueous liquid medium for at least about 20 days at 55° C.;
substantially stable for at least about 60 minutes at about 121'C.' under retort processing conditions;
substantially stable to hot fill, pasteurization conditions;
substantially stable in the presence of an aqueous liquid medium for at least about 300 days at 20° C.:
substantially stable to HTST processing conditions; or
substantially stable to UHT processing conditions.

28. A water stable pharmaceutical gel composition according to claim 27, wherein the gel composition is substantially stable in the presence of an aqueous liquid medium for at least about 20 days at 55° C.

29. A water stable pharmaceutical gel composition according to claim 27, wherein the gel composition is substantially stable for at least about 60 minutes at about 121° C. under retort processing conditions.

30. A water stable pharmaceutical gel composition according to claim 27, wherein the gel composition substantially stable in the presence of an aqueous liquid medium for at least about 300 days at 20° C.

31. A water stable pharmaceutical gel composition according to claim 27, wherein the gel composition is substantially stable to hot fill pasteurization conditions.

32. A water stable pharmaceutical gel composition according, to claim 28, wherein the gel composition is substantially stable to HTST processing conditions.

33. A water stable pharmaceutical gel composition according to claim 27, wherein the gel composition is substantially stable to UHT processing conditions.

34. A water stable pharmaceutical gel composition according to claim 28, wherein the gel composition is substantially stable to at. least two conditions selected from the group consisting of:
at least about 20 days at 55° C. in the presence of an aqueous liquid medium;
at least about 60 minutes at about 121° C. under retort processing conditions;
at least about 300 days at 20° C. in the presence of an aqueous liquid medium;
hot fill pasteurization conditions;
HTST processing conditions; and
UHT processing conditions.

35. A liquid form oral pharmaceutical composition according to claim 19, wherein the liquid form oral pharmaceutical composition is:
  substantially stable in the presence of an aqueous liquid medium for at least about 20 days at 55° C.;
  substantially stable for at least about 60 minutes at about 121° C. under retort processing; conditions;
  substantially stable to hot fill pasteurization conditions;
  substantially stable in the presence of an aqueous liquid medium for at least about 300 days at 20° C.;
  substantially stable to HTST processing conditions; or
  substantially stable to UHT processing conditions.

36. A kit according to claim 23, wherein the kit is:
  substantially stable in the presence of an aqueous liquid medium for at least about 20 days at 55° C.;
  substantially stable for at least about 60 minutes at about 121° C. under retort processing conditions:
  substantially stable to hot fill pasteurization conditions;
  substantially stable in the presence of an aqueous liquid medium for at least about 300 days at 20° C.;
  substantially stable to HTST processing conditions; or
  substantially stable to UHT processing conditions.

37. A rehydration beverage composition according to claim 25, wherein the rehydration beverage composition is:
  substantially stable in the presence of an aqueous liquid medium for at least about 20 days at 55° C.:
  substantially stable for at least about 60 minutes at about 121° C. under retort processing conditions;
  substantially stable to hot fill pasteurization conditions;
  substantially stable in the presence of an aqueous liquid medium for at least about 300 days at 20° C.:
  substantially stable to HTST processing conditions; or
  substantially stable to UHT processing conditions.

38. A liquid form oral pharmaceutical composition according to claim 19, wherein the liquid form oral pharmaceutical composition is suitable for oral delivery of the therapeutic agent.

39. A liquid form oral pharmaceutical composition comprising:
  a water stable pharmaceutical composition according to claim 26;
  a pharmaceutically acceptable aqueous liquid medium;
  wherein the liquid form oral pharmaceutical composition is:
    substantially stable in the presence of an aqueous liquid medium for at least about 20 days at 55° C.;
    substantially stable for at least about 60 minutes at about 121° C. under retort processing conditions;
    substantially stable to hot till pasteurization conditions;
    substantially stable in the presence of an aqueous liquid medium for at least about 300 days at 20° C.;
    substantially stable to HTST processing conditions; or
    substantially stable to UHT processing conditions.

40. A rehydration beverage composition, comprising:
  a water stable pharmaceutical composition according to claim 26;
  a pharmaceutically acceptable aqueous liquid medium; and
  optionally at least one mineral or non-mineral nutritional supplement;
  wherein the aqueous medium comprises an isotonic solution; and
  wherein the rehydration beverage composition is:
    substantially stable in the presence of an aqueous liquid medium for at least about 20 days at 55° C.;
    substantially stable for at least about 60 minutes at about 121° C. under retort processing conditions;
    substantially stable to hot fill pasteurization conditions;
    substantially stable in the presence of an aqueous liquid medium for at least about 300 days at 20° C.;
    substantially stable to HTST processing conditions; or
    substantially stable to UHT processing conditions.

41. A water stable pharmaceutical composition of claim 7, wherein more than about 50% by weight of the therapeutic agent is present in the pharmaceutical composition as a therapeutic agent:cyclodextrin complex.

42. A water stable pharmaceutical composition of claim 2, wherein the molar ratio of anti-inflammatory agent to cyclodextrin is from about 1:2 to about 2:1.

43. A water stable pharmaceutical composition of claim 2, wherein the molar ratio of anti-inflammatory agent to cyclodextrin is from about 1:1.5 to about 1.5:1.

* * * * *